(12) United States Patent
Xu et al.

(10) Patent No.: US 7,807,472 B2
(45) Date of Patent: Oct. 5, 2010

(54) METHODS FOR SEPARATION AND DETECTION OF KETOSTEROIDS AND OTHER CARBONYL-CONTAINING COMPOUNDS

(75) Inventors: Xia Xu, Frederick, MD (US); Regina G. Ziegler, Bethesda, MD (US); David J. Waterhouse, Frederick, MD (US); Joseph E. Saavedra, Thurmont, MD (US); Larry K. Keefer, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1400 days.

(21) Appl. No.: 10/511,409

(22) PCT Filed: Apr. 15, 2003

(86) PCT No.: PCT/US03/11562

§ 371 (c)(1),
(2), (4) Date: Oct. 13, 2004

(87) PCT Pub. No.: WO03/089921

PCT Pub. Date: Oct. 30, 2003

(65) Prior Publication Data

US 2005/0181514 A1    Aug. 18, 2005

Related U.S. Application Data

(60) Provisional application No. 60/372,848, filed on Apr. 15, 2002.

(51) Int. Cl.
*G01N 33/00* (2006.01)
*G01N 1/00* (2006.01)

(52) U.S. Cl. .......... 436/87; 436/173; 436/817; 435/287.1

(58) Field of Classification Search .......... 436/164–172, 436/87, 173, 817; 435/287.1
See application file for complete search history.

(56) References Cited

U.S. PATENT DOCUMENTS 5,272,134 A * 12/1993 Berliner .......... 512/3
(Continued)

FOREIGN PATENT DOCUMENTS

WO    WO03089921 A1    10/2003

OTHER PUBLICATIONS

Takadate et al., A Convenient Derivatization with Anion Exchange Resin Catalysts for High-Performance Liquid Chromatographic Analysis. I. Derivatization of Estrogens with Dansyl Chloride, Chem. Pharm. Bull, vol. 33, No. 11, pp. 5092-5095, 1985.*
(Continued)

*Primary Examiner*—Krishnan S Menon
*Assistant Examiner*—Rebecca Fritchman
(74) *Attorney, Agent, or Firm*—Woodcock Washburn LLP

(57) ABSTRACT

Methods for enhancing detection by mass spectroscopy (MS) and/or chromatographic separability of carbonyl-containing compounds such as steroids are disclosed. Reaction of a carbonyl compound with a sulfonhydrazide compound provides a sulfonhydrazone with enhanced ionization efficiency during the electrospray ionization process. In a particularly disclosed embodiment, derivatization of catechol estrogens with p-toluenesulfonhydrazide enhances both detection by atmospheric pressure ionization-MS (API-MS), such as electron spray ionization-MS (ESI-MS) and separation by liquid chromatography (such as HPLC) under reverse phase conditions. In yet other embodiments, the sulfonhydrazone is further reacted with a sulfonyl halide under alkaline conditions to derivatize hydroxyl groups in the compound. Prior formation of the sulfonhydrazide derivative protects the carbonyl bond of the compound during subsequent alkaline reaction with the sulfonyl halide.

17 Claims, 25 Drawing Sheets

Analysis for Catechol Estrogens by LC-ESI-MS

U.S. PATENT DOCUMENTS

| | | | |
|---|---|---|---|
| 5,807,748 A * | 9/1998 | Bailey | 436/89 |
| 6,326,209 B1 | 12/2001 | Jia et al. | |
| 6,541,263 B2 | 4/2003 | Gao | |
| 2005/0181514 A1 | 8/2005 | Xu et al. | |

OTHER PUBLICATIONS

Barry et al., "Use of S-pentafluorophenyl tris(2,4,6-trimethoxyphenyl)phosphonium acetate bromide and (4-hydrazino-4-oxobutyl) tris(2,4,6-trimethoxyphenyl)phosphonium bromide for the derivatization of alcohols, aldehydes and ketones for detection by liquid chromatography/electrospray mass spectrometry," *Rapid Commun. Mass Spectrom* 17(5):484-97, 2003. (abstract).

"Handbook of Derivatives for Chromatography," $2^{nd}$ Edition, Ed. Blau and Halket, John Wiley & Sons Ltd., West Sussex, England, 1993, pp. 4, 131, 157-1746.

Choi et al., "Rapid HPLC-electrospray tandem mass spectrometric assay for urinary testosterone and dihydrotestosterone glucuronides from patients with benign prostate hyperplasia," *Clin. Chem.* 49(2):322-5, 2003.

Dalvie and O'Donnell, "Characterization of polar urinary metabolites by ionspray tandem mass spectrometry following dansylation," *Rapid Commun. Mass Spectrom.* 12(8):419-22, 1998.

Frei-Häusler and Frei, "Determination of hydroxybiphenyls as dansyl derivatives," *Journal of Chromatography* 79:209-216, 1973.

Fotsis and Adlercreutz, "The multicomponent analysis of estrogens in urine by ion exchange chromatography and GC-MS—I. Quantitation of estrogens after initial hydrolysis of conjugates," *J. Steroid Biochem.* 28(2):203-13, 1987.

Ghulam et al., "Quantitative analysis of human serum corticosterone by high-performance liquid chromatography coupled to electrospray ionization mass spectrometry," *J. Chromatogr. B. Biomed Sci. Appl.* 30;727(1-2):227-33, 1999. (abstract).

Görög, "The changing face of chemical derivatization in pharmaceutical and biomedical analysis," *Fresenius J. Anal. Chem.* 362:4-8, 1998.

Halperin et al., "A new method for determination of serum cholestanol by high-performance liquid chromatography with ultraviolet detection," *Journal of Chromatography B.,* 742:345-352, 2000.

Hammermeister et al., "Characterization of dansylated glutathione, glutathione disulfide, cysteine and cystine by narrow bore liquid chromatography/electrospray ionization mass spectrometry," *Rapid Commun. Mass Spectrom.* 14(6):503-8, 2000.

Jeannot et al., "Determination of endocrine-disrupting compounds in environmental samples using gas and liquid chromatography with mass spectrometry," *J. Chromatogr. A.* 974(1-2):143-59, 2002. (abstract).

Johnson et al., "A rapid screening procedure for cholesterol and dehydrocholesterol by electrospray ionization tandem mass spectrometry," *J. Lipid Res.* 42(10):1699-705, 2001. (abstract).

Kempter et al., "Determination of carbonyls using liquid chromatography-mass spectrometry with atmospheric pressure chemical ionization," *J. Environ. Monit..* 1(4):307-11, 1999. (abstract).

Kim et al., "Determination and excretion study of gestrinone in human urine by high performance liquid chromatography and gas chromatography/mass spectrometry," *Rapid Commun. Mass Spectrom.* 14(14):1293-300, 2000.

Kim et al., "Determination of the metabolites of gestrinone in human urine by high performance liquid chromatography, liquid chromatography/mass spectrometry and gas chromatography/mass spectrometry," *Rapid Commun. Mass Spectrom.* 14(18):1717-26, 2000.

Lai et al., "Rapid monitoring assay of congenital adrenal hyperplasia with microbore high-performance liquid chromatography/electrospray ionization tandem mass spectrometry from dried blood spots," *Rapid Commun. Mass Spectrom.* 15(22):2145-51, 2001. (abstract).

Lee et al., "Estrogens in female thyroid cancer: alteration of urinary profiles in pre- and post-operative cases," *Cancer Letters* 189:27-32, 2003.

Ma and Kim, "Determination of steroids by liquid chromatography/mass spectrometry," *J. Am. Soc. Mass Spectrom* 8:1010-1020, 1997.

Mitamura et al., "Studies on neurosteroids XII. Determination of enzymatically formed catechol estrogens and guaiacol estrogens by rat brains using liquid chromatography-mass spectrometry-mass spectrometry," *Journal of Chromatography B.* 748:89-96, 2000.

Mitamura et al., "Studies on neurosteroids. Part XIII. Characterization of catechol estrogens in rat brains using liquid chromatography-mass spectrometry-mass spectrometry," *Analyst.* 125(5):811-4, 2000.

Mitamura and Shimada, "Derivatization in liquid chromatography/mass spectrometric analysis of neurosteroids," *Se Pu* 19(6):508-12, 2001. (abstract).

Moody et al., "Determination of buprenorphine in human plasma by gas chromatography-positive ion chemical ionization mass spectrometry and liquid chromatography-tandem mass spectrometry," *J. Anal. Toxicol.* 21(6):406-14, 1997. (abstract).

Ohno et al., "Specific determination of urinary 6beta-hydroxycortisol and cortisol by liquid chromatography-atmospheric pressure chemical ionization mass spectrometry," *J. Chromatogr. B. Biomed Sci. Appl.* 746(1):95-101, 2000.

Shackelton et al., "Electrospray mass spectrometry of testosterone esters: potential for use in doping control," *Steroids* 62:523-529, 1997.

Shimada et al., "Gas chromatography and high-performance liquid chromatography of natural steroids," *J. Chromatogr. A.* 935(1-2):141-72, 2001.

Singh et al., "Liquid chromatography/electron capture atmospheric pressure chemical ionization/mass spectrometry: analysis of pentafluorobenzyl derivatives of biomolecules and drugs in the attomole range," *Anal. Chem.* 72(14):3007-13, 2000.

Tang et al., "Simultaneous determination of urinary free cortisol and 6beta-hydroxycortisol by liquid chromatography-atmospheric pressure chemical ionization tandem mass spectrometry and its application for estimating hepatic CYP3A induction," *J. Chromatogr. B. Biomed Sci. Appl.* 742(2):303-13, 2000.

Tjernberg et al., "Screening of eltanolone metabolites in dog urine by anion-exchange/reversed-phase liquid chromatography and mass spectrometry," *J. Chromatogr. B. Biomed. Sci. Appl.* 715(2):395-407, 1998. (abstract).

Visser et al., "High-performance liquid chromatography of the neuroactive steroids alphaxalone and pregnanolone in plasma using dansyl hydrazine as fluorescent label: application to a pharmacokinetic-pharmacodynamic study in rats," *J. Chromatogr. B. Biomed. Sci. Appl.* 745(2):357-63, 2000.

Wolthers and Kraan, "Clinical applications of gas chromatography and gas chromatography-mass spectrometry of steroids," *J. Chromatogr. A.* 843(1-2):247-74, 1999.

Wu et al., "Simultaneous quantitative determination of norgestrel and progesterone in human serum by high-performance liquid chromatography-tandem mass spectrometry with atmospheric pressure chemical ionization," *Analyst.* 125(12):2201-5, 2000. (abstract).

Xu et al., "Menstrual cycle effects on urinary estrogen metabolites," *The Journal of Clinical Endocrinology & Metabolism* 84(11):3914-3918, 1999.

Xu et al., "Analysis of endogenous estrogen metabolites in postmenopausal urine by HPLC-electrospray ionization-tandem mass spectrometry, Abstract," *Proceedings of the $50^{th}$ Annual Meeting of the ASMS,* Apr. 15, 2002. (abstract).

Xu et al., "Stable isotope dilution high-performance liquid chromatography-electrospray ionization mass spectrometry method for endogenous 2- and 4-hydroxyestrones in human urine," *J. Chromatogr. B. Analyt. Technol. Biomed Life Sci.* 780(2):315-30, 2002.

Xu et al., "Measuring Seven Endogenous Ketolic Estrogens Simultaneously in Human Urine by High-Performance Liquid Chromatography-Mass Spectrometry," *Anal. Chem.* 76(19):5829-5836, 2004.

Yahioglu et al., "8-(ω-aminoalkyl)theophyllines and their use in preparing fluorescently labeled derivatives for applications in immunoassay," *Bioconjugate Chem.* 8:611-616, 1997.

Yamada et al., "A new sensitive determination method of estradiol in plasma using peroxyoxalate ester chemiluminescence combined with an HPLC system," *Biomed. Chromatogr.* 14(5):333-7, 2000.

Yoshino et al., "Use of the derivatizing agent 4-aminobenzoic acid 2-(diethylamino)ethyl ester for high-sensitivity detection of oligosaccharides by electrospray ionization mass spectrometry," *Anal. Chem.* 67(21):4028-31, 1995. (abstract).

Ziegler et al., "Quantifying estrogen metabolism: an evaluation of the reproducibility and validity of enzyme immunoassays for 2-hydroxyestrone and 16alpha-hydroxyestrone in urine," *Environ. Health Perspect.* 105(Suppl 3):607-14, 1997.

Zwiener et al., "Method optimization for the determination of carbonyl compounds in disinfected water by DNPH derivatization and LC-ESI-MS-MS," *Anal. Bioanal. Chem.* 372(5-6):615-21, 2002. (abstract).

Adlercruetz, H., et al., "Estrogen metabolism and excretion in oriental and caucasian women," J. Natl. Cancer Inst., 1994, 86(14), 1076-1082.

Adlercreutz, H., et al., "An isotope dilution gas chromatographic-mass spectrometric method for the simulataneous assay of estrogens and phytoestrogens in urine," J. Steroid Biochem. & Mol. Biol., 2004, 92(5), 399-411.

Anari, et al., "Derivatization of ethinylestradiol with dansyl chloride to enhance electrospray ionization: application in trace analysis of ethinylestradiol in rhesus monkey plasma," Anal. Chem., 2002, 74, 4136-4144.

Answers.com, "Blood plasma: definition and much more for answers.com," http://www.answers.com/topic/blood-plasma, downloaded from the internet on Nov. 11, 2005, 4 pages.

Ball, P., et al., "Radioimmunoassay of 2-hydroxyesterone and 2-methoxyestrone in human urine," Steroids, 1979, 33 (5), 563-576.

Banks, J.T., et al., "Thermal and photochemical fragmentation of a,a-dialkoxybenzyl radicals:a comparison of the thermal reactions with laser induced fragmentations by using laser flash and laser-jet photolyses," J. Am. Chem. Soc., 1993, 115, 2473-2477.

Banwell, M.G., et al., "Generation and solution-phase behaviour of some 2-halogeno-1,3-ring-fused cyclopropenes," J. Chem. Soc. Perkin Trans. 1, 1993, 945-963.

Beatson, G.T., "On the treatment of inoperable cases of carcinoma of the amma: suggestions for a new method of treatment, with illustrative cases," Lancet, 1896, 2, 104-107.

Bradlow, H.L., et al., "Application of an improved ELISA assay to the analysis of urinary estrogen metabolites," Steroids, 1998, 63, 406-413.

Cavalieri, E.L., et al., "Molecular origin of cancer: catechol estrogen-3,4-quinones as endogenous tumor initiators," proc. Natl. Acad. Sci. USA, 1997, 94, 10937-10942.

Clemons, M., et al., "Estrogen and the risk of breast cancer," N. Engl. J. Med., 2001, 344, 276-285.

Colditz, G.A., "Relationship between estrogen levels, use of hormone replacement thereapy, and breast cancer," J. Natl. Cancer Inst., 1998, 90(11), 814-823.

Dumitrescu, R.G., et al., "Understanding breast cancer risk-where do we stand in 2005?," J. Cell Mol. Med., 2005, 9(1), 208-221.

Emons, G., et al., "Radioimmunoassay for 4-hydroxyoestrone in human urine," Acta Endocinology, 1981, 97, 251-257.

Fenn, J.B., et al., "Electrospray ionization-principles and practice," Mass Spectrom. Rev., 1990, 9, 37-70.

Fishman, J., et al., "Biological properties of 16 a-hydroxyestrone: implications in estrogen physiology and pathophysiology," J. Clin. Endocrinol. Metab., 1980, 51(3), 611-615.

Getens, G., et al., "Nanotechnology in bio/clinical analysis," J. Chromatogr. B, 2000, 739, 139-150.

Kaaks, R., "Endogenous hormone metabolism as an exposure marker in breast cancer chemoprevention studies," IARC Sci. Publ., 2001, 154, 149-162.

Key, T.J.A., et al., "A prospective study of urinary oestrogen excretion and breast cancer risk," Br. J. of Cancer, 1996, 73, 1615-1619.

Klug, T.L., et al., "Monoclonal antibody-based enzyme immunoassay for simultaneous quantitation of 2- and 16 alpha-hydroxyestrone in urine," Steroids, 1994, 59, 648-655.

Lee, A.J., et al., "Characterization of the NADPH-dependent metabolism of 17B-estradol to multiple metabolites by human liver microsomomes and selectively expressed human cytochrome P450 3A4 and 3A5," J. Pharmacology & Experimental Therapeutics, 2001, 298(2), 420-432.

Makela, S.K., et al., "Nonspecificity of a direct 17 a-hydroxyprogesterone radioimmunoassay kit when used with samples for neonates," Clin. Chem., 1988, 34(10), 2070-2075.

McGuinnes, B.J., et al., "Radioimmunoassay of 2-hydroxyestrone in urine," Clin. Chem., 1994, 40, 80-85.

Nelson, et al., "Liquid chromatography-tandem mass spectrometry assay for simultaneous measurement of estradiol and estrone in human plasma," Clin. Chem., 2004, 50(2), 373-384.

Numazawa, M., et al., "Radioimmunoassay of 2-hydroxyesterone using antisera raised against antigenic complexes obtained by convenient methods," Chem. Pharm. Bull., 1989, 37, 1561-1563.

Pike, M.C., et al., "Estrogens, progestogens, normal breast cell proliferation, and breast cancer risk," Epidemiol. Rev., 1993, 15, 17-35.

Shimada, K., et al., "Studies on steroids: CLXV. Determination of isomeric catechol estrogens in pregnancy urine by high performance liquid chromatography with electrochemical detection," J. Chromatogr., 1981, 223, 33-39.

Shimada, K., et al., "Studies on steroids: CCXXIX. Separation and characterization of catechol oestrogen glucuronides in urine of pregnant woman by high-performance liquid chromatography," J. Chromatogr., 1987, 400, 215-221.

Shou, et al., "Development and validation of a high-sensitivity liquid chromatography/tandem mass spectrometry (LC/MS/MS) method with chemical derivatization for the determination of ethinyl estradiol in human plasma," Biomed. Chromatogr., 2004, 18(7), 414-421.

Suzuki, E., et al., "Assay of enzymic O-methylation of catechol oestrogens by high-performance liquid chromatography with coulometric detection," J. Chromatogr., 1993, 617, 221-225.

Todorovic, R., et al., "Analysis of potential biomarkers of estrogen-initiated cancer in the urine of syrian golden hamsters treated with 4-hydroxyestradiol," Carcinogenesis, 2001, 22, 905-911.

Toniolo, P.G., et al., "A prospective study of endogenous estrogens and breast cancer in postmenopausal women," J. of the Natl. Cancer Inst., 1995, 87(3), 190-197.

Travis, R.C., et al., "Oestrogen exposure and breast cancer risk," Breast Cancer Res., 2003, 5, 239-247.

Wong, T., et al., "identification of the steroids in neonatal plasma that interfere with 17 alpha-hydroxprogesterone radioimmunoassay," Clin. Chem., 1992, 38(9), 1830-1837.

Wudy, S.A., "Determination of dehydroepiandrosterone sulfate in human plasma by gas chromatography/mass spectrometry using a deuterated internal standard: a method suitable for routine clinical use," Horm. Res., 1993, 39, 235-240.

Xu, X., et al., "Analysis of fifteen estrogen metabolites using packed column supercritical fluid chromatography—mass spectrometry," Anal. Chem., 2006, 78, 1553-1558.

Xu, et al., "Measuring fifteen endogenous estrogens simultaneously in human urine by high-performance liquid chromatography-mass spectrometry," Anal. Chem., 2005, 77, 6646-6654.

Yager, J.D., et al., "Molecular mechanisms of estrogen carcinogenesis," Annu. Rev. Pharmacol. Toxicol., 1996, 36, 203-232.

Zhang, et al., "Quantitation of 17 a-ethylestradiol in aquatic samples using liquid-liquid phase extraction, dansyl derivatization and liquid chromatography/positive electrospray tandem mass spectrometry," Rapid Commun. Mass Spectrom., 2004, 18(22), 2739-2742.

* cited by examiner

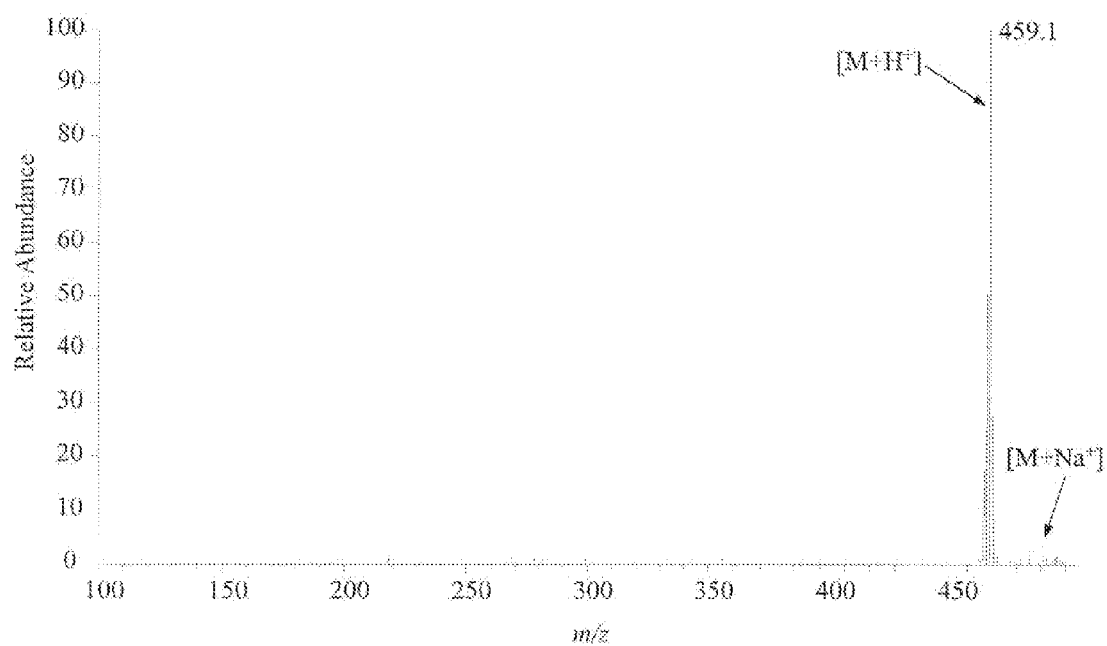

A) 2-hydroxyE1 calibration standard curve

B) 4-hydroxyE1 calibration standard curve

METHODS FOR SEPARATION AND DETECTION OF KETOSTEROIDS AND OTHER CARBONYL-CONTAINING COMPOUNDS

CROSS-REFERENCE TO RELATED APPLICATIONS

This is the U.S. National Stage of International Application No. PCT/US03/11562, filed Apr. 15, 2003, which was published under PCT Article 21(2), which in turn claims the benefit of U.S. Provisional Application No. 60/372,848 filed Apr. 15, 2002. Both of these prior applications are incorporated by reference herein.

FIELD

Methods of separating and detecting carbonyl-containing compounds, including ketosteroids, are disclosed.

BACKGROUND

Non-immunochemical qualitative and quantitative determinations of compounds found in biological samples often require separation of the compound of interest from others in the sample. Once separated, the compound of interest may be detected and/or identified by measuring some property of the compound.

Since many biological molecules have low volatilities and decompose when heated, rather than vaporizing to form gas phase molecules, separation by gas chromatography (GC) is often impossible without first preparing volatile derivatives. Therefore, high performance liquid chromatography (HPLC) is often chosen for separations of non-volatile biological molecules. In HPLC, separations are made in the liquid phase and derivatization is typically unnecessary because most molecules are soluble in at least one solvent.

Nonetheless, derivatization is useful in HPLC to enhance separation of molecules and to increase sensitivity of detection of the separated molecules. For example, the analyte molecules might not possess physical properties that can be accurately measured in the presence of solvent molecules. Detection of the analyte may be improved by derivatization with reagents to form readily detectable derivatives. For example, an analyte can be derivatized with a fluorescent compound to make it readily detectable.

Coupling a chromatographic method of separation with mass spectrometric detection permits separation of complex mixtures into their components, detection of the components, and identification of the components from their mass spectra. Since mass spectrometry (MS) requires conversion of analyte molecules to gas phase ions, coupling an HPLC column to a mass spectrometer requires a means of isolating the analyte molecules from excess liquid solvent as they emerge from the column. If the solvent were introduced into the vacuum of a mass spectrometer, the pressure increase would prevent the instrument from functioning. MS also requires that isolated analyte molecules be ionized before they can be detected. Electrospray ionization (ESI) is one method for coupling the effluent of an HPLC column to a mass spectrometer. ESI functions to remove solvent from a liquid sample without losing the analytes and to ionize the analytes.

In ESI, a stream of analyte-containing solvent is passed through a narrow capillary tube, the end of which is held at a high positive or negative electrical potential. The strong electric field that surrounds the end of the capillary tube causes the emerging liquid to leave the capillary as a fine mist of droplets. The droplets acquire an excess of charge (positive or negative depending upon the potential applied to the capillary) as they leave the capillary and enter an atmospheric pressure evaporation chamber (ESI is an example of an atmospheric pressure ionization, or API, method). As solvent continues to evaporate from the droplet the charge density in each droplet continues to increase. Eventually, repulsion between ions in the droplet exceeds the surface tension of the droplet and ions are expelled into the gas phase in a process termed ion evaporation. Before the analyte ions formed in the evaporation chamber are selectively introduced into the mass spectrometer, they collide with other ions and neutral molecules. During these collisions, charges may be transferred between species to form new ions and new neutral molecules in a process called chemical ionization.

In positive ion mode ESI (i.e. the capillary is held at a high positive potential), an important chemical ionization process is transfer of protons ($H^+$) between species in the evaporation chamber. Positive ion mode ESI is widely used for vaporizing and ionizing biological molecules because biological molecules typically have multiple sites in their structures that have an affinity for protons. Proteins, in fact, can attract and hold enough protons and other cations (e.g. $Na^+$) during the ESI process that they can form multiply charged ions. Smaller biological molecules, however, may not ionize efficiently, especially if they do not possess groups of atoms having an affinity for protons. Derivatization of such molecules offers one way to improve the efficiency of ionization in ESI and hence detection by MS.

In combined HPLC-ESI-MS, both separability in the HPLC column and detection by ESI-MS determine whether the method may be used to determine particular analytes. Derivatization to improve separation by HPLC can have a detrimental effect on detection by ESI-MS, and the converse is true, making it difficult to find appropriate derivatization schemes for HPLC-EIS-MS.

SUMMARY

Sensitive methods for measuring ketosteroids in biological samples are described. Derivatization of ketosteroids with a sulfonhydrazide compound improves both separation and detection of ketosteroids by mass spectrometry, such as ionization spectroscopy, for example API-MS such as HPLC-API-MS, and more particularly HPLC-ESI-MS. In a specific disclosed embodiment, derivatization with p-toluenesulfonhydrazide to form a p-toluenesulfonhydrazone compound is demonstrated to simplify separation and enhance detection of estrogens.

Sulfonhydrazide derivatization is also disclosed to improve ionization of carbonyl-bearing compounds under electrospray ionization conditions. Increased ionization efficiency improves detection in a mass spectrometer. For example, derivatization of catechol estrogens with p-toluenesulfonhydrazide makes it possible to quantify as little as 1 nanogram catechol estrogen in a 10 mL urine sample. At this level of quantitation, it is possible measure the low endogenous levels of catechol estrogens in urine from post-menopausal women.

In yet other embodiments, a second step derivatization is performed by derivatizing the ketosteroids under alkali conditions with a sulfonyl compound, such as a sulfonyl halide, for example sulfonyl chloride. The prior reaction with the sulfonhydrazide protects the carbonyl group against alkali conditions that can destroy the carbonyl group of the ketosteroids in the absence of such protection. Reaction with the sulfonyl compound provides a highly ionizable moiety that enhances their electron spray ionization efficiency and HPLC-ESI-MS sensitivity.

In yet another embodiment, the carbonyl groups of a ketosteroid are reacted with a carbonyl protecting reagent, and the hydroxyl groups are then reacted with a hydroxyl protecting reagent under alkali conditions. Protecting the carbonyl group of the steroids allows for the derivatization of the hydroxyl group without significant degradation, particularly alkali degradation. This two-step process of carbonyl and hydroxyl derivatizations provides better liquid chromatography separation of steroids, and allows for better signal detection in mass spectrometry, such as API-MS (for example ESI-MS), when at least one of the derivatization groups contains a highly ionizable moiety that enables ionization under either positive ion or negative ion modes of electrospray ionization.

BRIEF DESCRIPTION OF THE DRAWINGS

FIGS. 2A-D are ESI mass spectra of CE-TSH (A, B) and d-CE-TSH (C,D).

DETAILED DESCRIPTION OF DISCLOSED EMBODIMENTS

Figure 1:
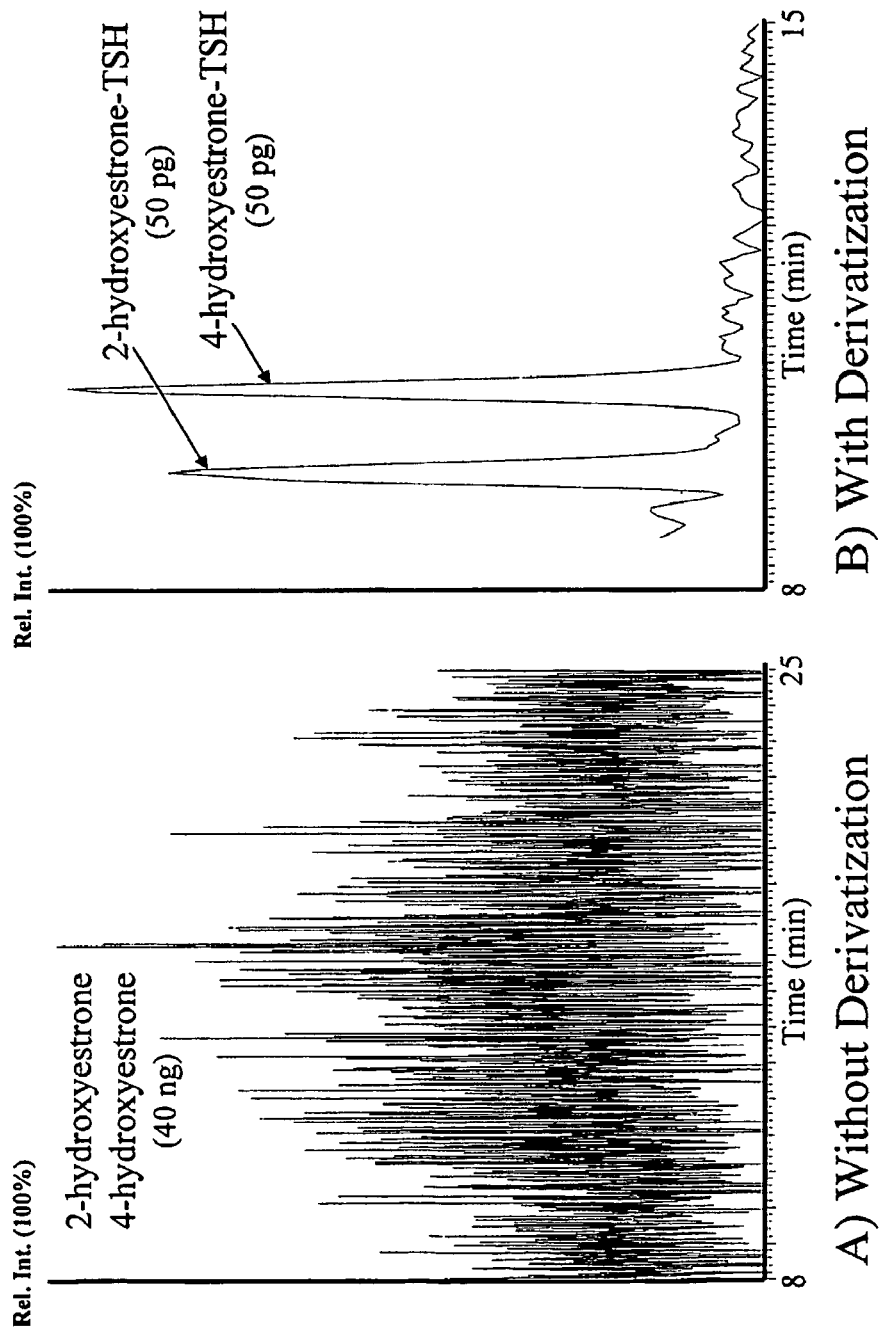
FIGS. 1A-B are HPLC ESI-MS chromatographic profiles for CE samples without (A) and with (B) sulfonhydrazide derivatization.
Figure 2A:
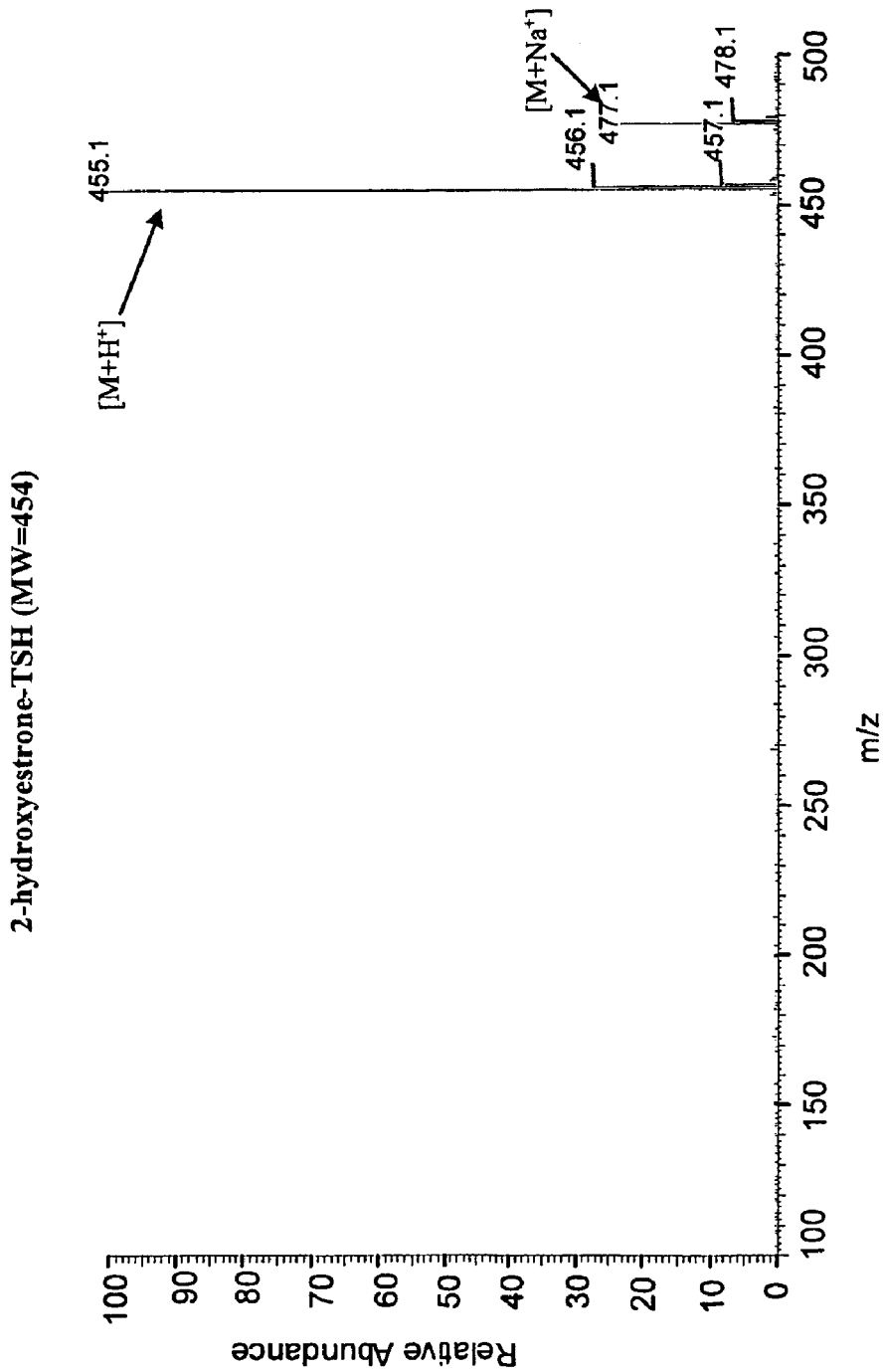
Figure 2B:
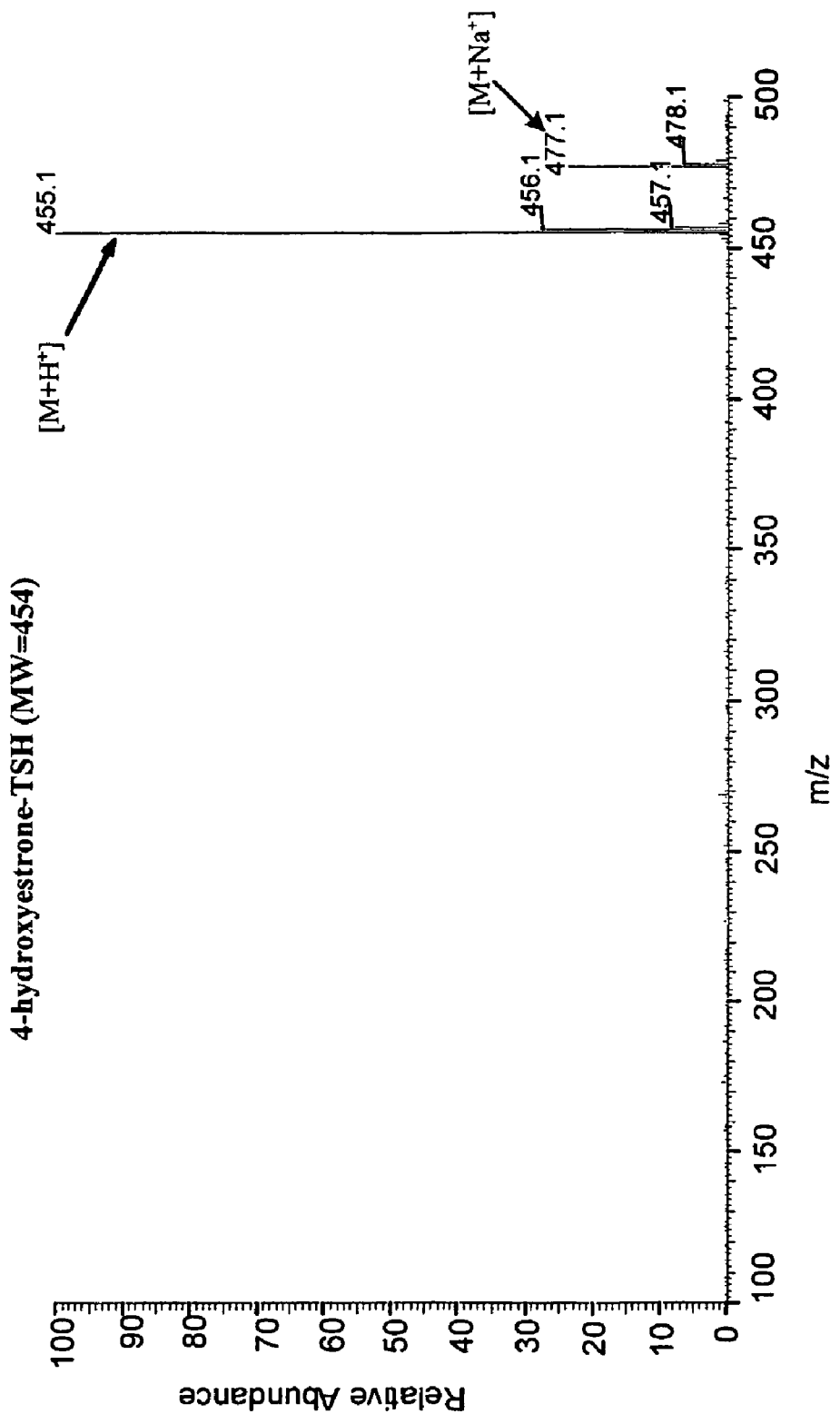
Figure 2C:
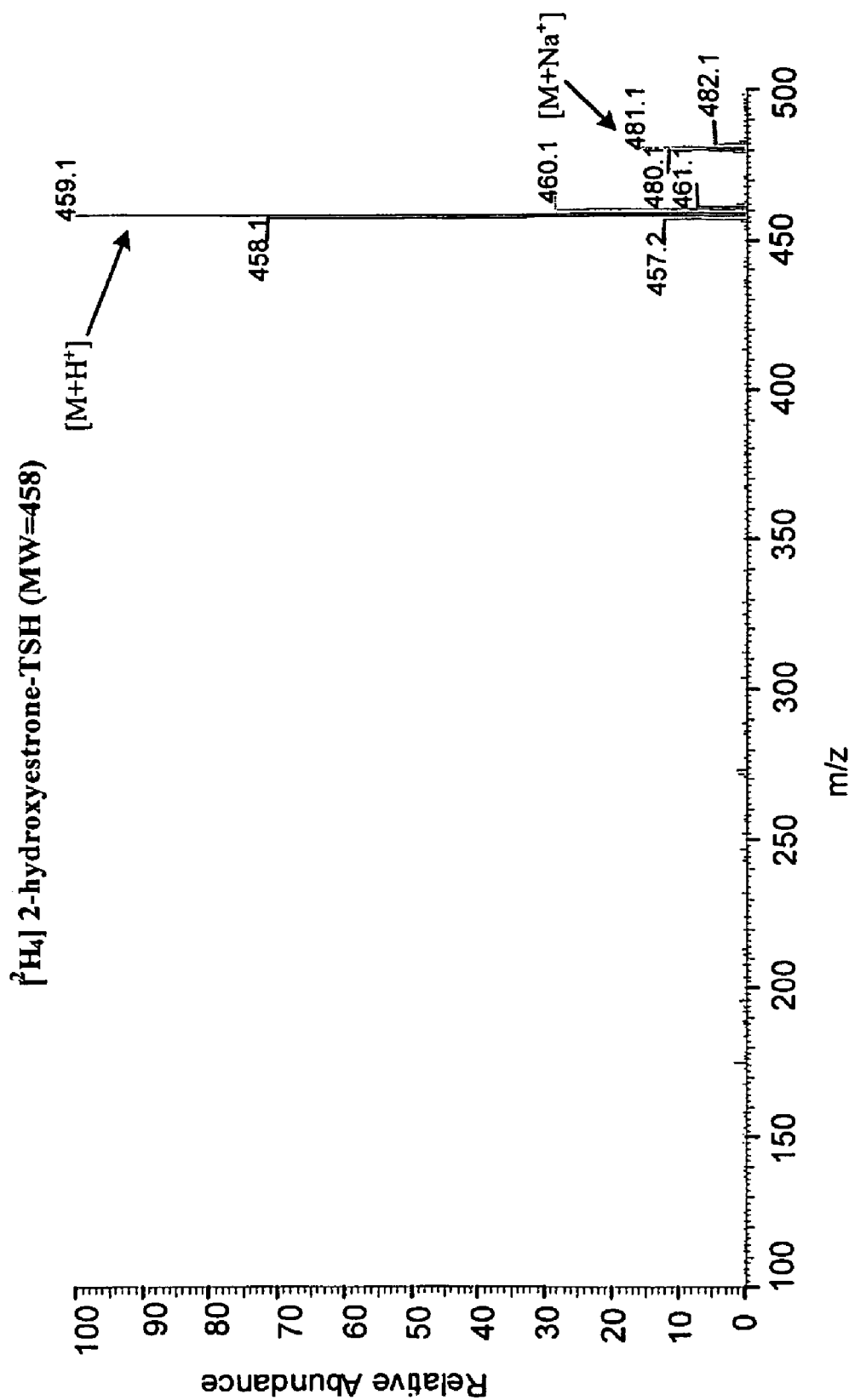
Figure 3A:
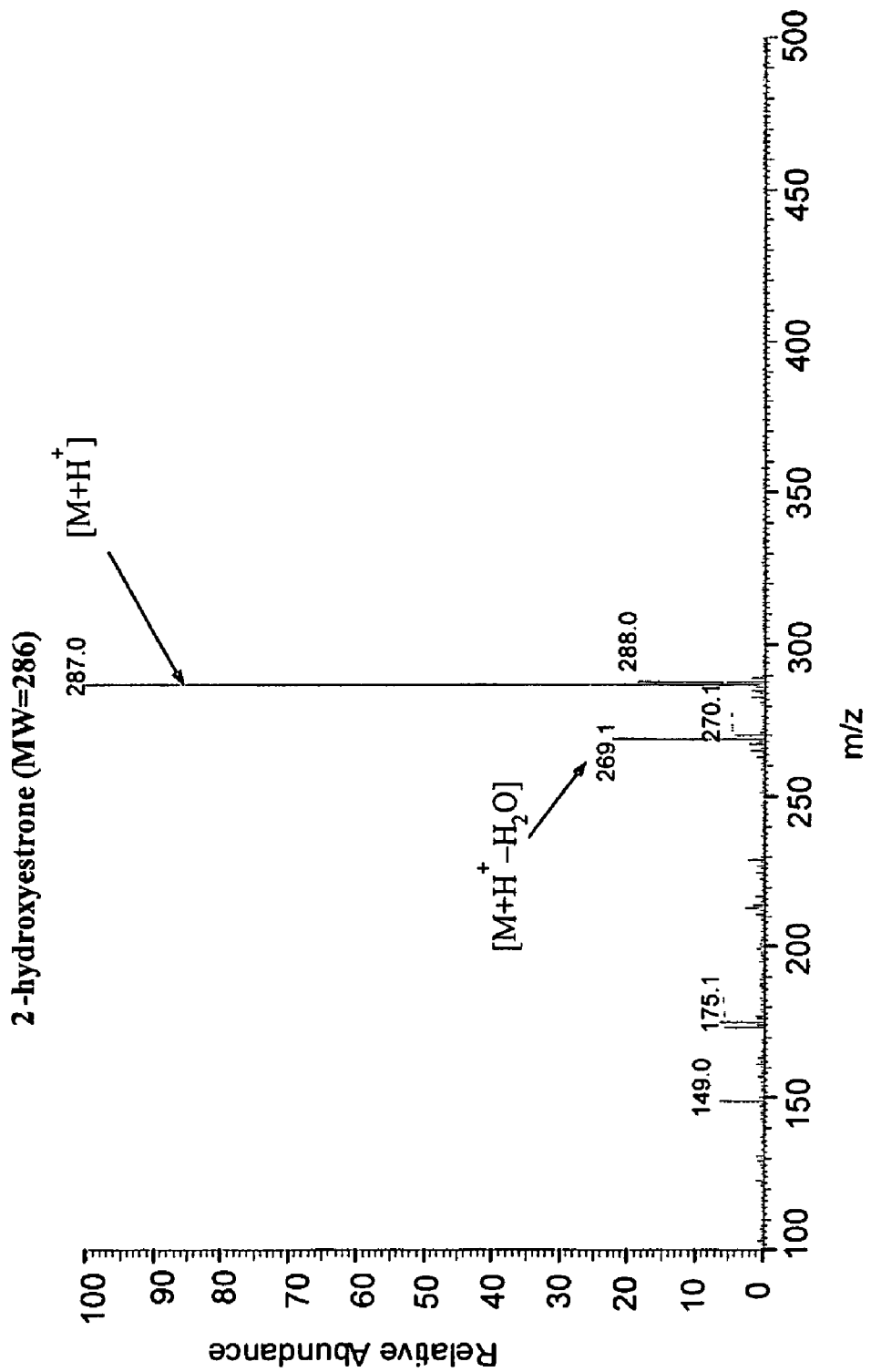
FIGS. 3A-D are APCI mass spectra for CE (A, B) and d-CE (C, D) without derivatization.
Figure 3B:
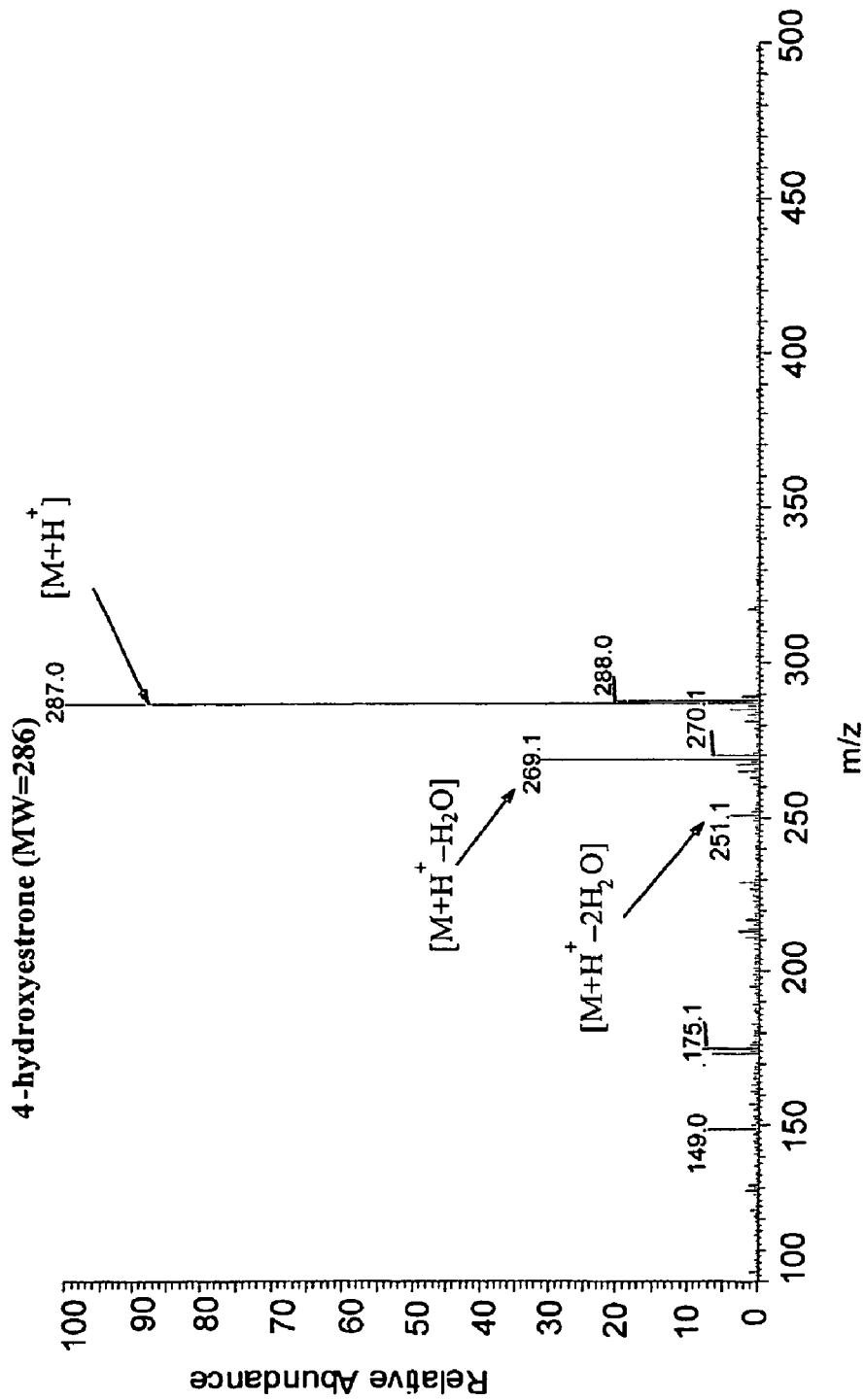
Figure 3C:
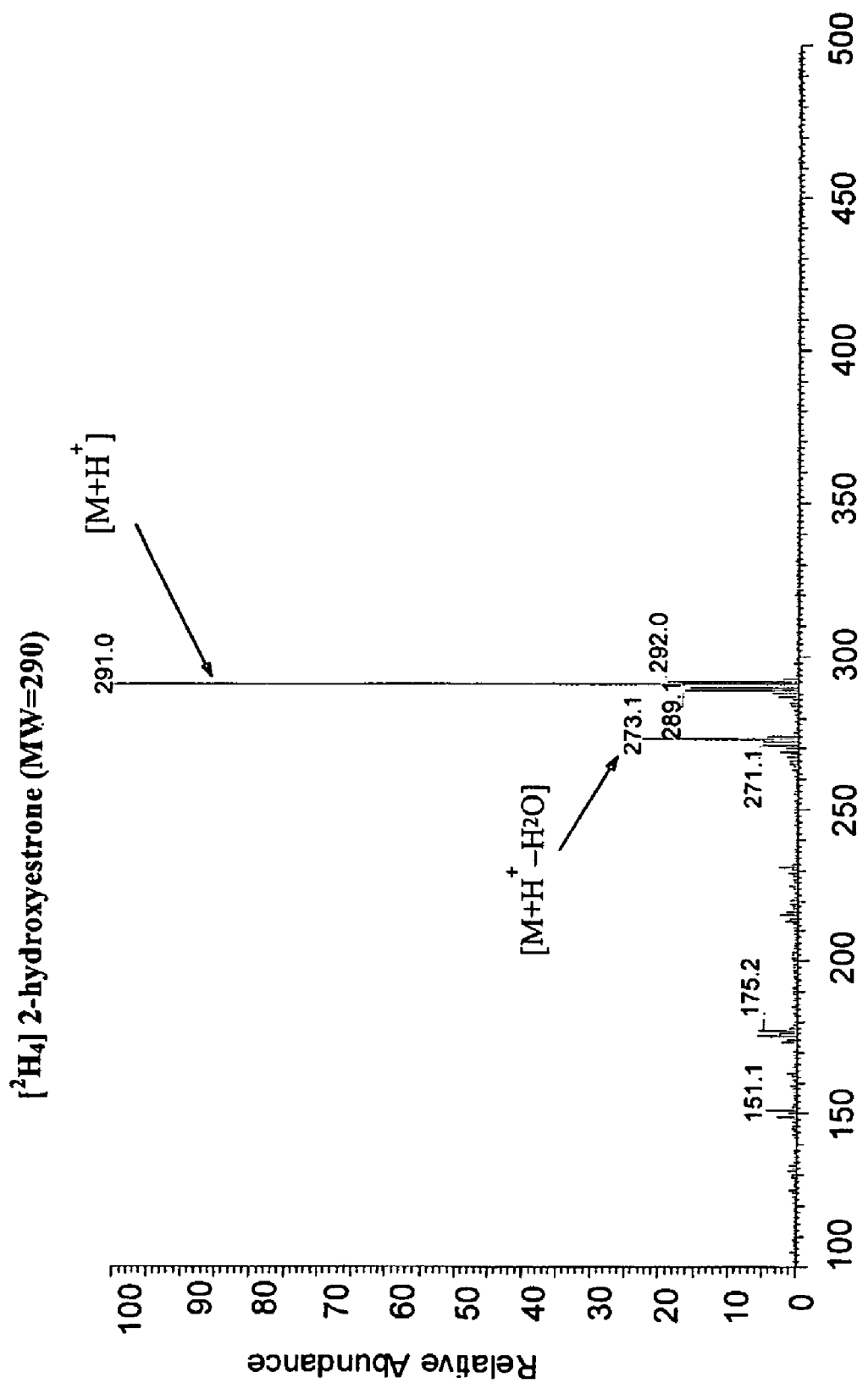
Figure 3D:
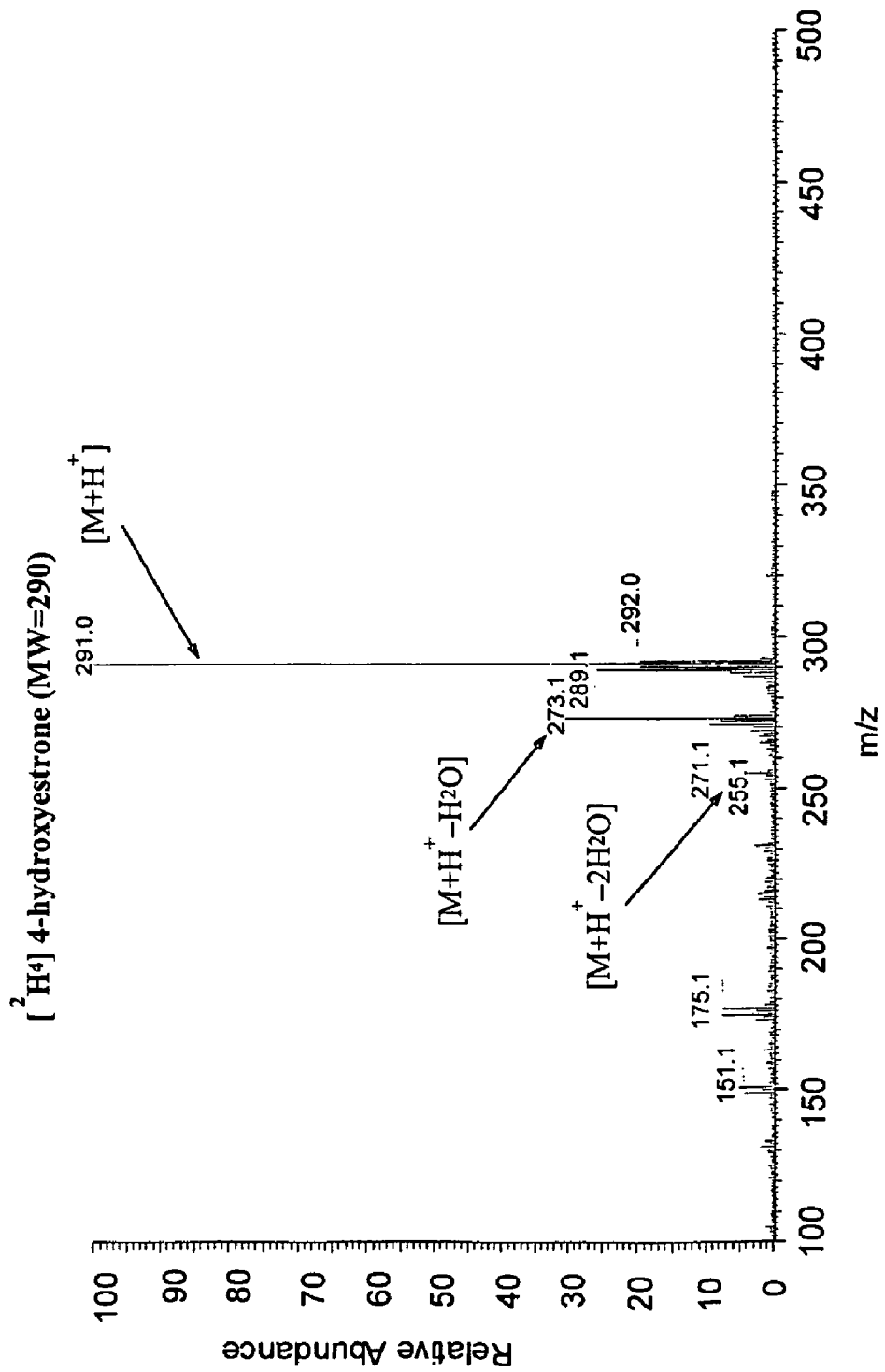

The following abbreviations and terms are collected here to aid the reader in understanding the description and examples which follow.

"a," "an," and "the" refer to one or more unless the context clearly indicates otherwise.

Alkaline conditions: Having a pH greater than 7. In some examples highly alkaline conditions are used, for example with a pH of greater than 9 or 10.

API: Atmospheric pressure ionization. This term includes (without limitation) both ESI and APCI.

HPLC—high performance liquid chromatography, a liquid chromatographic method of separation that includes the techniques of nano-LC and capillary HPLC.

ESI-MS—electrospray ionization mass spectrometry, which is a particular example of ionization spectroscopy.

LC-MS—liquid chromatography-mass spectrometry.

HPLC-ESI-MS—high performance liquid chromatography-electrospray ionization-mass spectrometry, a specific type of LC-MS in which ESI is the ionization method.

Ionization spectroscopy: Spectroscopy preceded by ionization of the analyte, for example by gas-phase ionization, electron ionization, chemical ionization (such as desorption chemical ionization), negative ion chemical ionization, and atmospheric pressure ionization (such as electrospray ionization and atmospheric chemical ionization).

APCI—atmospheric pressure chemical ionization, which is another example of an ionization method that can be used in ionization mass spectroscopy.

ketosteroid—a carbonyl-bearing steroid.

catechol estrogens (CE)—genotoxic estrogen metabolites having an aromatic ring bearing two hydroxyl groups.

dCE—deuterated analogs of catechol estrogens.

carbonyl-bearing compond—a compound having as part of its structure a carbon-oxygen double bond.

TSH—p-toluenesulfonhydrazide.

CE-TSH—catechol estrogens derivatized with p-toluenesulfonhydrazide.

dCE-TSH—deuterated catechol estrogen derivatized with p-toluenesulfonhydrazide.

detecting—a qualitative and/or quantitative measurement of a compound in a sample.

SIM—single ion monitoring.

Chromatographic separation: A separation method that depends upon the different rates at which various substances moving in a stream (mobile phase) are retarded by a stationary material (stationary phase) as they pass over it. In liquid chromatography, the mobile phase is liquid. Higher performance liquid chromatography (HPLC) refers to systems which obtain excellent resolution by forcing the mobile phase under pressure through a long, usually thin column. Examples of HPLC pressures are 350-1500 psi, although the pressure may be higher (for example as high as 10,000 psi).

Sulfonhydrazide derivative: A compound produced by reaction with a sulfonhydrazide reagent.

Sulfonyl halide derivative: A compound produced by reaction with a sulfonyl halide.

A method is disclosed for detecting ketosteroids by reacting a ketosteroid in a sample with a sulfonhydrazide compound to form a sulfonhydrazone of the ketosteroid and analyzing the reacted sample by positive ion mode electrospray ionization mass spectrometry. The determination may be either qualitative or quantitative and is based on detecting the sulfonhydrazone of the ketosteroid. The ketosteroid may be separated from other components in the sample by HPLC, either before or after derivatization, and analysis by API-MS (for example EIS-MS) is facilitated by derivatization. Chormatography, such as liquid chromatography, for example HPLC, may be performed under reverse phase (polar solvent/non-polar stationary phase) conditions to further facilitate API detection. For example, HPLC separation may be accomplished by an isocratic or gradient elution with a methanol/water solvent system and a C18 stationary phase. Useful gradient systems include a gradient from 20:80 methanol/water to 80:20 methanol/water, for example, a gradient from 25:75 to 75:25 methanol/water, such as a gradient from 40:60 to 60:40 methanol/water. In some embodiments, the ketosteroid is extracted from the sample to provide a concentrated sample for analysis.

A method for enhancing the positive ion mode electrospray ionization efficiency of a carbonyl compound is also disclosed. This method includes reacting a carbonyl compound with a sulfonhydrazide to form a sulfonhydrazone of the carbonyl-containing compound. Sulfonhydrazones are efficiently ionized by electrospray ionization processes making them more easily detected by mass spectrometry. Sulfonhydrazide derivatization is particularly effective for increasing the ESI-MS signal of ketosteroids, such as androgens, corticoids, estrogens, sterols, vitamin D metabolites, phytosteroids, neurosteroids and bile acids, and combinations thereof. In a disclosed embodiment, derivatization of catechol estrogens with p-toluenesulfonhydrazide particularly improves their ESI-MS detection.

Examples of sulfonhydrazide compounds useful for forming detectable derivatives of carbonyl-containing compounds have the structure

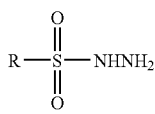

wherein R is selected from the group consisting of alkyl (such as C1-C10 alkyl, for example C1-C5 alkyl), substituted alkyl, aryl, and substituted aryl.

In some embodiments, the sulfonhydrazide may have the structure

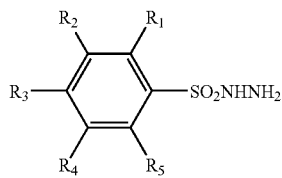

wherein $R_1$-$R_5$ are independently selected from the group consisting of hydrogen, C1-C5 alkyl, C1-C4 alkoxy, halogen, amino, nitro, hydroxyl, carbonyl, nitroso, cyano, and sulfonyl, and combinations thereof. One example of a sulfonhydrazide having this structure is p-toluenesulfonhydrazide.

Methods for separating and detecting ketosteroids in a biological sample, such as a blood, urine, or tissue sample, are also provided. A ketosteroid may be extracted from a biological sample to provide a concentrated sample of the ketosteroid, which is then reacted with p-toluenesulfonhydrazide to form a p-toluenesulfonhydrazone product of the ketosteroid. Separation of the p-toluenesulfonhydrazone product of the ketosteroid from other components in the concentrated sample is conveniently accomplished by chromatography, such as liquid chromatography, for example reverse phase HPLC. The ketosteroid may be detected in the HPLC effluent by API-MS (such as ESI-MS). Advantageously, the p-toluenesulfonhydrazone product provides an intense ESI-MS signal that may be used to determine the presence and/or amount of the ketosteroid in the sample. In particular embodiments, quantitation of the ketosteroid is facilitated by a stable-isotope dilution method where a known amount of a deuterated analog of the ketosteroid is added to the biological sample prior to extracting the ketosteroid and used as an internal standard. The ketosteroid in the sample is quantified by comparing the intensity of the ESI-MS signals from the ketosteroid and its deuterated analog. In a disclosed embodiment the method is applied to determine the amount of estrogen, specifically catechol estrogen, in a urine sample. Derivatization with p-toluenesulfonhydrazine also facilitates separation under convenient reverse phase HPLC condition, such as a methanol/water mobile phase and a C18 stationary phase.

For convenience, predetermined amounts of reagents and equipment employed to carry out the methods of the disclosure may be provided together in a kit in packaged combination. A kit can comprise in packaged combination (a) a sulfonhydrazide compound and (b) other reagents and equipment for determining the amount of ketosteroid in a sample. Such other reagents and equipment include those described in Example 1 below. For example, a kit for determining the presence of a ketosteroid can include a sulfonhydrazide compound and a deuterated standard of the ketosteroid in packaged combination. In some embodiments, the kit may also include a sulfonyl halide, such as sulfonyl chloride.

The effect of derivatization with a sulfonhydrazide compound on detectability of compounds by ESI-MS is dramatically illustrated in FIGS. 1A and 1B. FIG. 1A shows that no ESI-MS signal is observed for catechol estrogens (CE) as they elute from the HPLC column without derivatization. FIG. 1B shows that with derivatization well-resolved and symmetrical peaks corresponding to elution of the catechol estrogens are observed.

The following examples are provided to aid understanding of the disclosure and are not meant to limit the scope of the invention in any way.

Example 1

HPLC-ESI-MS Determination of Catechol Estrogens

In this example, a stable isotope dilution HPLC-ESI-MS method is described. The method includes a simple and rapid derivatization step that greatly improves method sensitivity and HPLC separability of catechol estrogens (CE), making LC-MS a much more competitive method for human endogenous catechol estrogen analysis.

A critical role for endogenous estrogen in the development of breast cancer has been postulated for more than a century, ever since Beatson demonstrated that oophorectomy induced tumor remission in human breast cancer (Beatson, *Lancet*, 2: 104, 1896). Substantial evidence supports a causal relationship between risk of human breast cancer and levels of endogenous estrogen (see, for example, Colditz, *J. Natl. Cancer Inst.*, 90: 814, 1998). Increased risk has been reported in women with high serum and urine estrogens (see, for example, Toniolo et al., *J. Natl. Cancer Inst.*, 87: 190, 1995), as well as in those women exposed to increased estrogen levels over time as a result of late menopause, early onset of menstruation and/or postmenopausal obesity (see, for example Henderson et al., *Cancer Res.*, 73: 1615, 1996). A key mechanism in estrogen-related breast cancer may be the metabolic activation of estrogens to genotoxic metabolites called catechol estrogens (see, for example, Yager and Liehr, *Annu. Rev. Pharmacol. Toxicol.*, 36: 203, 1996) mainly 2-hydroxyestrone and 4-hydroxyestrone in humans. This process is shown below.

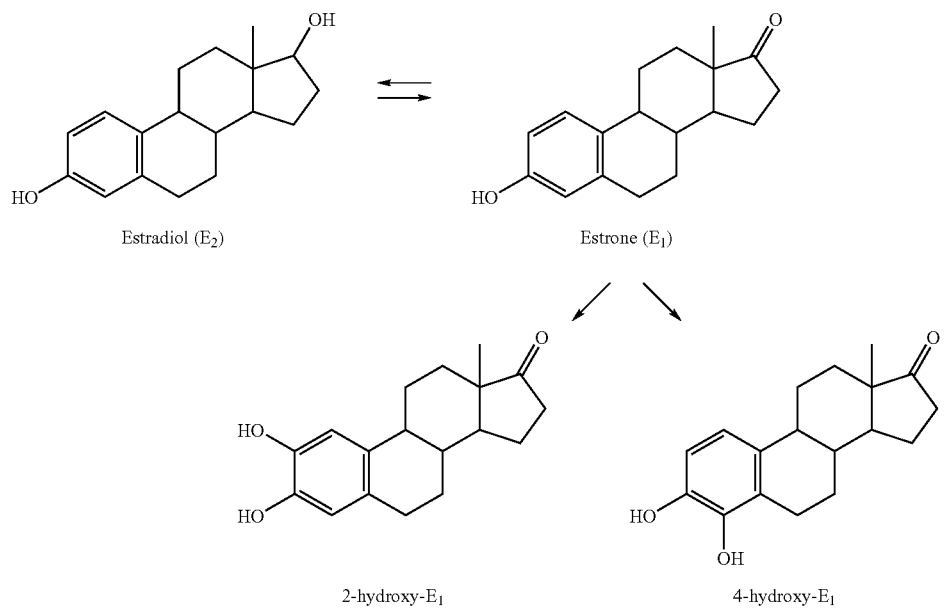

Estradiol (E₂) ⇌ Estrone (E₁)

2-hydroxy-E₁     4-hydroxy-E₁

Electrophilic quinone products of these catechol estrogens can react with DNA to form both stable and depurinating adducts known to generate mutations and cell transformation that can initiate cancers (see, for example, Cavalieri et al., *Proc. Natl. Acad. Sci. USA*, 94: 10937, 1997). It is believed that quantitative measurement of endogenous catechol estrogens will play an important role in elucidating the mechanism of breast carcinogenesis and in estimating the risk of breast cancer in individual women.

Current methods for measuring endogenous catechol estrogens most often involve radioimmunoassay (RIA) (see, for example Ball et al., *Steroids*, 33: 563, 1979; Emons et al., *Acta Endocrinol.*, 97: 251, 1981; and McGuinness et al., *Clin. Chem.*, 40: 80, 1994), enzyme immunoassay (EIA) (see, for example, Klug et al., *Steroids*, 59: 648, 1994), high-performance liquid chromatography (HPLC) with electrochemical detection (see, for example, Shimada et al., *J. Chromatogr.*, 223: 33, 1981), and stable isotope dilution gas chromatography-mass spectrometry (GC-MS) (see, for example, Fotsis and Aldercreutz, *J. Steroid Biochem.*, 28: 203, 1987).

RIA and EIA suffer from relatively poor specificity due to the cross-reactivity of antibodies (see, for example, Ziegler et al., *Environ. Health Perspect*, 105(3): 607, 1997). HPLC with electrochemical detection has been used for catechol estrogen analysis in hamsters treated with catechol estrogens and in pregnant women, whose estrogen levels are elevated at least 10-fold. The stable isotope dilution GC-MS method is both sensitive and specific, and has been successfully used not only for urine samples from non-pregnant premenopausal women but also for urine from postmenopausal women, in which catechol estrogens are substantially reduced. However, the stable isotope dilution GC-MS method requires extensive and laborious sample preparation, including three $C_{18}$ solid phase extractions, six ion-exchange column separations, four liquid-liquid extractions, and two derivatization procedures for each urine sample. Although liquid chromatography-mass spectrometry (LC-MS) has been used for in vitro and in vivo pharmacological studies of catechol estrogens in rat brains (see, for example, Mitamura et al., *Analyst*, 125: 811, 2000), the sensitivity of LC-MS with either electrospray ionization (ESI) or atmospheric pressure chemical ionization (APCI) is not adequate for the endogenous levels of catechol estrogens in women (see, Ma and Kim, *J. Am. Soc. Mass Spectrom.*, 8; 1010, 1997).

A. Chemicals and Reagents

Catechol estrogens (CE), 2-hydroxyestrone (2-hydroxyE₁) and 4-hydroxyestrone (4-hydroxyE₁), were obtained from Steraloids, Inc. (Newport, R.I., USA). Deuterium-labeled catechol estrogens (d-CE), [²H₄] 2-hydroxyestrone and [²H₄] 4-hydroxyestrone, were purchased from C/D/N Isotopes, Inc. (Pointe-Claire, Quebec, Canada). The structures of each of these compounds are shown below. All CE and d-CE analytical standards had a purity of ≧98%.

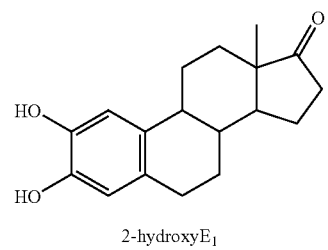

2-hydroxyE₁

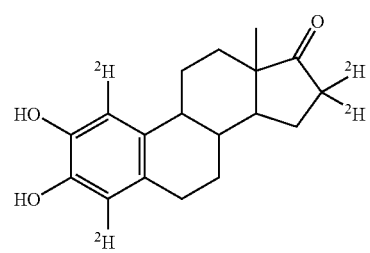

[²H₄]-2-hydroxyE₁

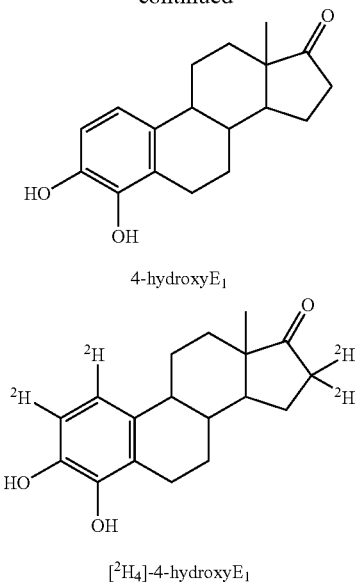

4-hydroxyE$_1$

[$^2$H$_4$]-4-hydroxyE$_1$ p-Toluenesulfonhydrazide (TSH) was purchased from Aldrich Chemical Co. (Milwaukee, Wis., USA). Methanol (HPLC grade) and formic acid (reagent grade) were obtained from EM Science (Gibbstown, N.J., USA), and water (HPLC grade) was obtained from Mallinckrodt Baker, Inc. (Paris, Ky., USA). Glacial acetic acid (HPLC grade), L-ascorbic acid (reagent grade), boric acid (reagent grade), sodium bicarbonate (reagent grade) and sodium hydroxide (reagent grade) were purchased from J. T. Baker (Phillipsburg, N.J., USA), and sodium acetate (reagent grade) was purchased from Fisher Scientific (Fair Lawn, N.J., USA). β-Glucuronidase/sulfatase from *Helix pomatia* (Type H-2) and QAE Sephadex A-25 were obtained from Sigma Chemical Co. (St. Louis, Mo., USA). All glassware, including Pasteur pipettes, was silanized (Aqua-Sil, Pierce, Rockford, Ill., USA). QAE-Sephadex gels in acetate and borate forms were prepared as described in Fotsis and Adlercreutz, *J. Steroid Biochem.*, 28: 203, 1987.

B. Urine Sample Collection

Twenty-four-hour urine samples were collected in three-liter bottles containing 3 g ascorbic acid, to prevent oxidation, from two healthy non-pregnant premenopausal women (aged 34 and 38 years) and two healthy postmenopausal women (aged 58 and 60 years; 5+ years past last menstrual cycle). None of the women was taking exogenous estrogens. For the two premenopausal women, samples were collected during the midfollicular (days 8-9 of menstrual cycle) and midluteal phases (6 days before the anticipated menses) of the menstrual cycle. Immediately after the urine collection was completed, urine volume was recorded and sodium azide, to prevent bacterial growth, was added to achieve a 0.1% (w/v) concentration. One half of the 24-h urine from each of two postmenopausal women was mixed to prepare a pooled postmenopausal urine, and the remaining two halves were non-pooled postmenopausal urines. Similarly, pooled and non-pooled premenopausal urines during either midfollicular or midluteal phase were prepared. Aliquots of both pooled and non-pooled urines were stored at −80° C. until analysis.

C. Preparation of Stock and Working Standard Solutions

Stock solutions of CE and d-CE were each prepared at 80 μg ml$^{-1}$ by addition of 2 mg catechol estrogen powders to a volumetric flask and diluting to 25 ml with 100% methanol. These solutions were stored at −20° C. until needed to prepare working standard solutions. During each day of analysis, working standards of CE and d-CE were prepared by serial dilutions of stock solutions with 100% methanol. For the analyses, d-CE working standard solution was prepared at 800 ng ml$^{-1}$, while CE working standard solutions were prepared at 800 and 50 ng ml$^{-1}$.

D. Preparation of Calibration Standards

CE are naturally present at various levels in all human urine samples, including those from males. Therefore, use of CE-spiked urine to generate calibration curves was impractical. Non-biologic matrix calibration standards were prepared by combining 50 μl of the d-CE working internal standard solution (40 ng d-CE) with various volumes of CE working standard solution, which typically ranged from 0.5 to 64 ng CE.

E. Urinary CE Hydrolysis and Extraction Procedure

To a 10-ml aliquot of urine sample, 50 μl of the d-CE working internal standard solution (40 ng d-CE) was added, followed by 10 ml of freshly prepared enzymatic hydrolysis buffer containing 50 mg of L-ascorbic acid, 100 μl of β-glucuronidase/sulfatase from *Helix pomatia* (Type H-2) and 10 ml of 0.15 M sodium acetate buffer (pH 4.1). The sample was incubated overnight at 37° C. After hydrolysis, the sample was applied to a primed C$_{18}$ column (Bond Elut LRC, Chrom Tech, Inc., Apple Valley, Minn., USA) and washed with 5 ml of water. CE and d-CE were eluted with 3 ml of methanol and further purified on QAE-Sephadex in acetate and borate forms, respectively, as described by Fotsis and Adlercreutz.

F. Derivatization Procedure

The fraction containing both CE and d-CE was evaporated to dryness under nitrogen gas (Reacti-Vap III™, Pierce, Rockford, Ill., USA) and derivatized to form the CE and d-CE p-toluenesulfonhydrazones (CE-TSH and d-CE-TSH, respectively) by reaction with 400 μg p-toluenesulfonhydrazide (TSH) in 200 μl methanol and heating at 60° C. (Reacti-Therm III™ Heating Module, Pierce, Rockford, Ill., USA) for 30 min. Calibration standard mixtures were derivatized in the same way. These reactions are represented below. After derivatization, urine samples and calibration standards were evaporated to dryness under nitrogen and redissolved in 100 μl methanol for LC-MS analysis. The reactions that produce the TSH derivatives are shown below.

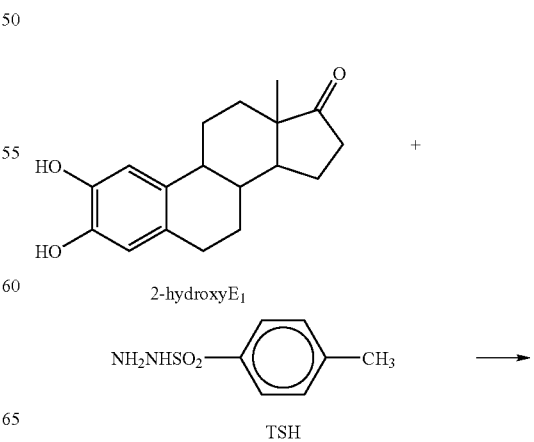

2-hydroxyE$_1$

TSH

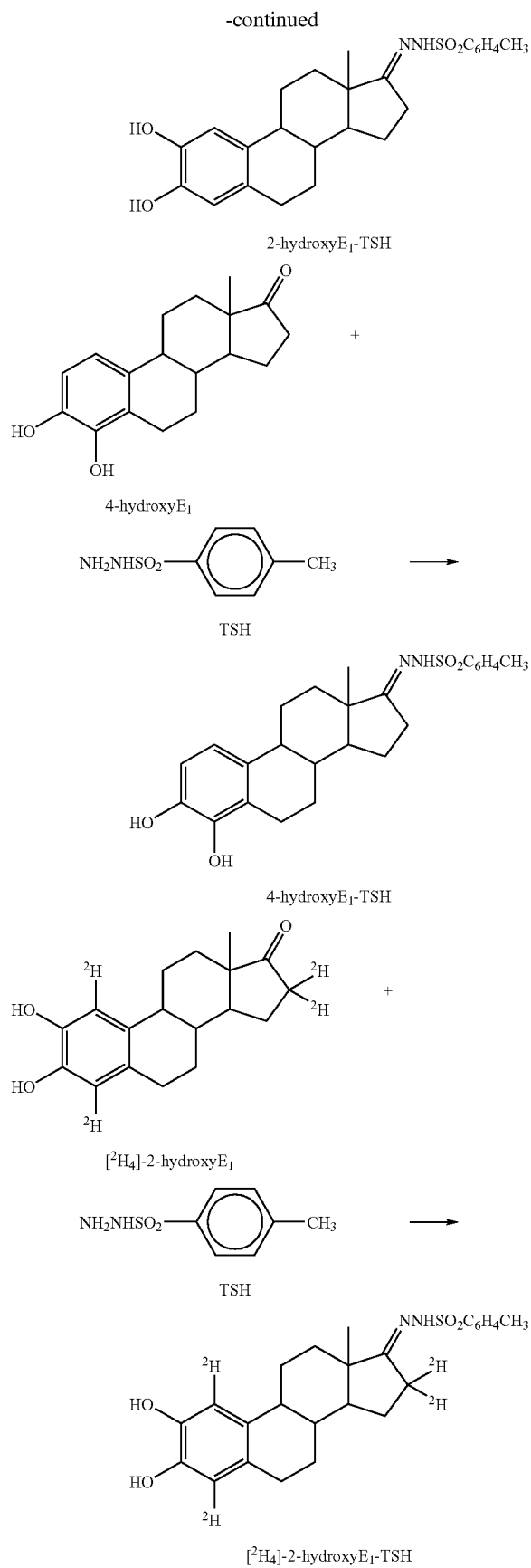
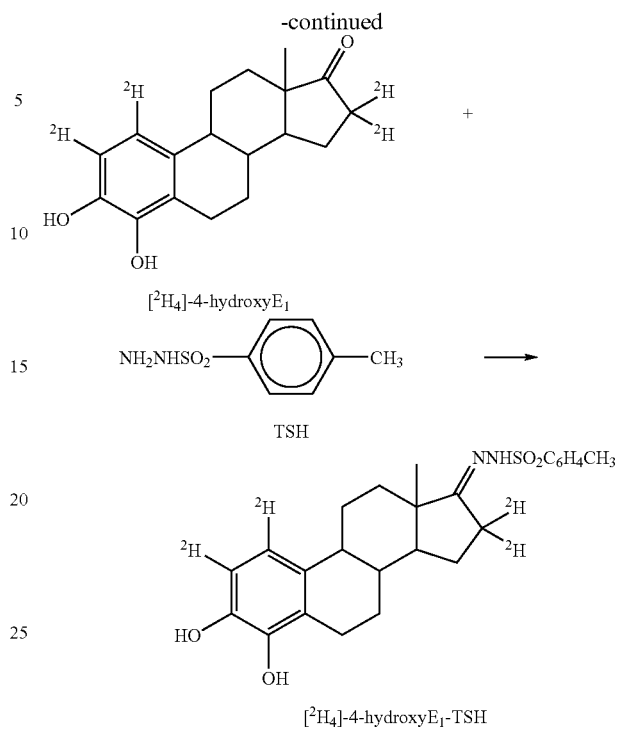

G. HPLC-MS

LC-MS analysis was performed on a Finnigan LCQ™ DECA ion trap mass spectrometer with Surveyor HPLC system (ThermoFinnigan, San Jose, Calif., USA) controlled by the Xcalibur software. Liquid chromatography was carried out on a reverse phase Luna C18(2) column (150×2.0 mm, 3 μm; Phenomenex, Torrance, Calif., USA). The mobile phase consisted of methanol as solvent A and water with 0.1% (v/v) formic acid as solvent B. The LC flow rate of 200 μl/min was used for both ESI and APCI modes. Sensitivity was such that only 5 μl of each 100-μl sample was injected by autosampler for analysis. The entire chromatography effluent was passed into the mass spectrometer interface for subsequent detection.

For the analysis of CE-TSH and d-CE-TSH, a linear gradient of A/B changing from 60:40 to 75:25 in 15 min was employed. After changing back from 75:25 to 60:40 in 2 min, the mobile phase composition A/B stayed at 60:40 for 8 min before the next injection. The ESI positive ion mode was used as follows: ion source voltage, 5 kV; heated capillary temperature, 250° C.; capillary voltage, 15 V; sheath gas flow rate, 70 units; auxiliary gas flow rate, 15 units; tube lens offset, 50 V. MS full scan mode was employed for characterizing mass spectra of CE-TSH and d-CE-TSH (FIGS. 2A-2D). These mass spectra were used to identify appropriate masses for detection of the compounds. MS selected ion monitoring (SIM) mode was used for the quantitative analysis. The protonated analyte ions [MH$^+$], m/z 455 and m/z 459, were monitored for CE-TSH and d-CE-TSH, respectively. The less abundant natriated analyte ions [MNa$^+$], about 15-20% of [MH$^+$], were used as the second ion pairs for confirming the analyte identification. Similar results were obtained for a simple isocratic elution solvent comprising 60% methanol/40% water with 0.1% (v/v) formic acid.

For the purpose of comparison, the LC-MS performance of CE and d-CE separation/detection without TSH derivatization were also examined. A linear gradient of A/B changing from 40:60 to 60:40 in 10 min was employed, and then held at 60:40 for an additional 10 min. After changing back from 60:40 to 40:60 in 2 min, the mobile phase composition A/B stayed at 40:60 for 8 min before the next injection. The APCI positive ion mode was used as follows: ion source current, 10 µA; vaporizer temperature, 450° C.; heated capillary temperature, 175° C.; capillary voltage, 15 V; sheath gas flow rate, 80 units; tube lens offset, 30 V. MS full scan mode was employed for characterizing the mass spectra of CE and d-CE (FIGS. 4A-D). MS SIM mode was used for the analysis of calibration standards without TSH derivatization. The protonated analyte ions [MH$^+$], m/z 287 and m/z 291, were monitored for CE and d-CE, respectively.

H. Quantitation of CE

CE-TSH/d-CE-TSH area ratios were determined for the SIM chromatographic peaks using the Xcalibur software. Calibration curves were constructed by plotting CE-TSH/d-CE-TSH peak area ratios obtained from calibration standards versus CE concentrations and fitting these data using linear regression. CE concentrations in urine samples were then interpolated using this linear function.

I. Absolute Recovery of CE After Hydrolysis and Extraction Procedure

To one set of six 10-ml aliquots of the pooled postmenopausal urine, 50 µl of the d-CE working internal standard solution (40 ng d-CE) was added, followed by the hydrolysis and extraction procedure described above. A second set of six 10-ml aliquots of the pooled postmenopausal urine was treated identically, except that the d-CE was added after the hydrolysis and extraction procedure instead of at the beginning. Both sets of samples were then derivatized and analyzed in consecutive LC-MS analyses. The absolute recovery of CE after the hydrolysis and extraction procedure was calculated by dividing the CE-TSH/d-CE-TSH peak area ratio from a sample of the second set with that from a comparable sample of the first set, and then calculating the mean of the six values.

J. Accuracy and Precision of the Urinary CE Analysis

To assess accuracy and intra batch precision of the method, 50 µl of the d-CE working internal standard solution (40 ng d-CE) was added to each of eighteen 10-ml aliquots of the pooled postmenopausal urine. Then, identical known amounts of CE (0, 8 or 30 ng, respectively) were added to each of six urine aliquots. All the urine samples were hydrolyzed, extracted, derivatized, and analyzed as described above. The endogenous CE concentration for the pooled postmenopausal urine was determined as the mean of the measured values from the six blank samples. This baseline CE concentration was then subtracted from the values determined for CE spiked urine samples to assess method accuracy and intra batch precision. In addition, duplicate aliquots of the pooled urines from both postmenopausal and premenopausal midluteal phase women were hydrolyzed, extracted, derivatized, and analyzed in four different batches to further assess the inter batch precision of the urinary CE analysis.

K. ESI and APCI Mass Spectra

The ESI mass spectra for CE-TSH and d-CE-TSH derivatives (more specifically the TSH derivatives of non-deuterated and deuterated 2-hydroxyE$_1$ and 4-hydroxyE$_1$) are presented in FIGS. 2A-D. These spectra are characterized by intense protonated analyte ions [MH$^+$] at m/z 455 and m/z 459 for CE-TSH and d-CE-TSH, respectively, and less abundant natriated analyte ions [MNa$^+$], about 15-20% of [MH$^+$], at m/z 477 and m/z 481 for CE-TSH and d-CE-TSH, respectively. Based on these data, the protonated analyte ions [MH$^+$] were monitored for quantitative analysis in SIM mode, and natriated analyte ions [MNa$^+$] were used as the second ion pairs for confirming the analyte identification. Note that little fragmentation is seen in these spectra, indicating that the TSH derivatives are stable under the ESI conditions.

Since the sensitivity of LC-MS analysis for CE and d-CE without derivatization is poor during ESI, the APCI mode was chosen for their analysis. The APCI mass spectra for CE and d-CE without derivatization are shown in FIGS. 3A-D. Unlike in the ESI mass spectra for CE-TSH and d-CE-TSH, the spectra of [MH$^+$-H$_2$O], [MH$^+$-2H$_2$O] and various steroid ring fragments were also observed in addition to [MH$^+$]. The protonated analyte ions [MH$^+$], m/z 287 and m/z 291, were monitored for CE and d-CE, respectively, during SIM mode analysis.

L. Importance of TSH Derivatization in CE Analysis

Figure 4A:
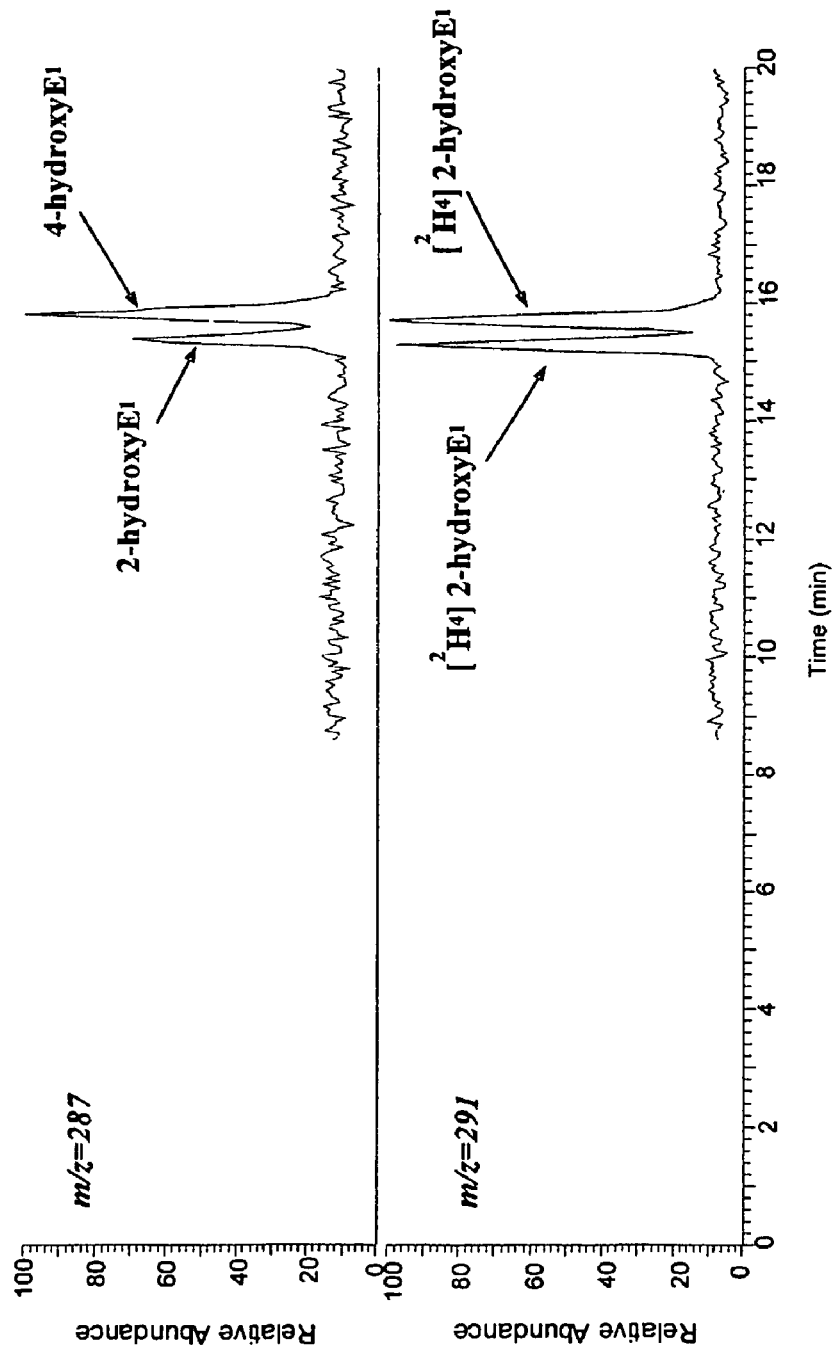
FIGS. 4A-B are HPLC chromatographic profiles (detected using single ion monitoring, SIM, at the indicated masses) of CE and d-CE without (A) and with (B) TSH derivatization.
Figure 4B:
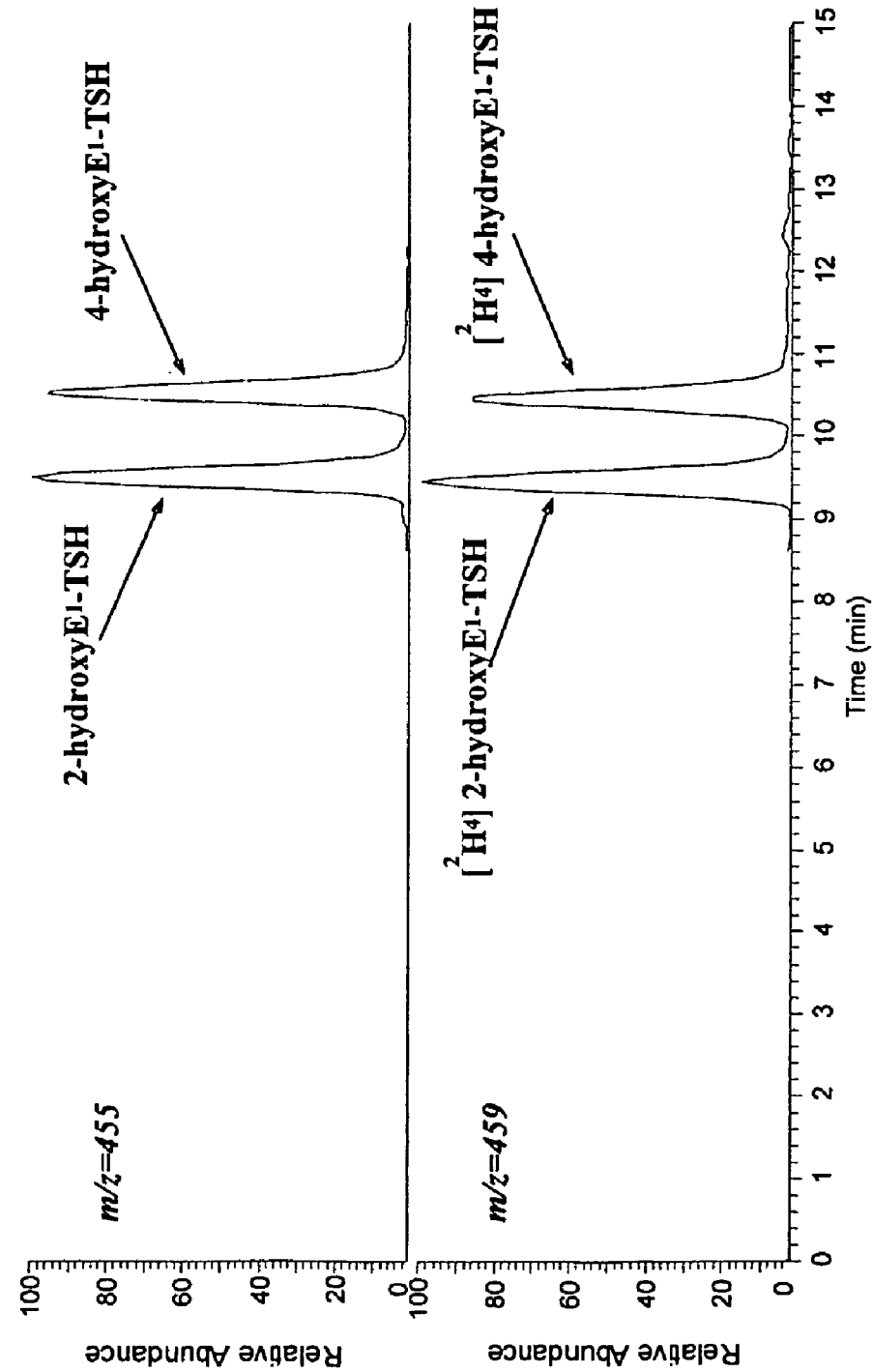

The success of TSH derivatization in CE analysis, and its importance is shown in FIGS. 4A and B. Comparison of FIGS. 4A and 4B reveals how TSH derivatization improved the peak separation and shortened the chromatography time. Within 11 min, baseline separation of 2-hydroxyE$_1$-TSH and 4-hydroxyE$_1$-TSH was achieved with a difference in retention times of more than 1 min, whereas underivatized 2-hydroxyE$_1$ and 4-hydroxyE$_1$ did not begin eluting until 15 min after injection and were still not fully separated, with a difference in retention times of less than 0.6 min, on the same C$_{18}$ column. Second, TSH derivatization improved HPLC column retention of the analytes. Therefore, a higher mobile phase methanol composition could be employed for chromatography of CE-TSH and d-CE-TSH, which improved the efficiency of the ESI process and enhanced method sensitivity, compared with CE and d-CE without derivatization. Third, TSH derivatization of CE and d-CE resulted in stable and intense protonated analyte ions [MH$^+$] with no fragmentation during their ionization process (see FIGS. 2A-D), which contributed to the improved sensitivity. Finally, the sulfonhydrazone in CE-TSH and d-CE-TSH has greater proton affinity than the ketone in CE and d-CE. This greatly enhanced the method sensitivity for ESI positive ion mode.

Figure 5A:
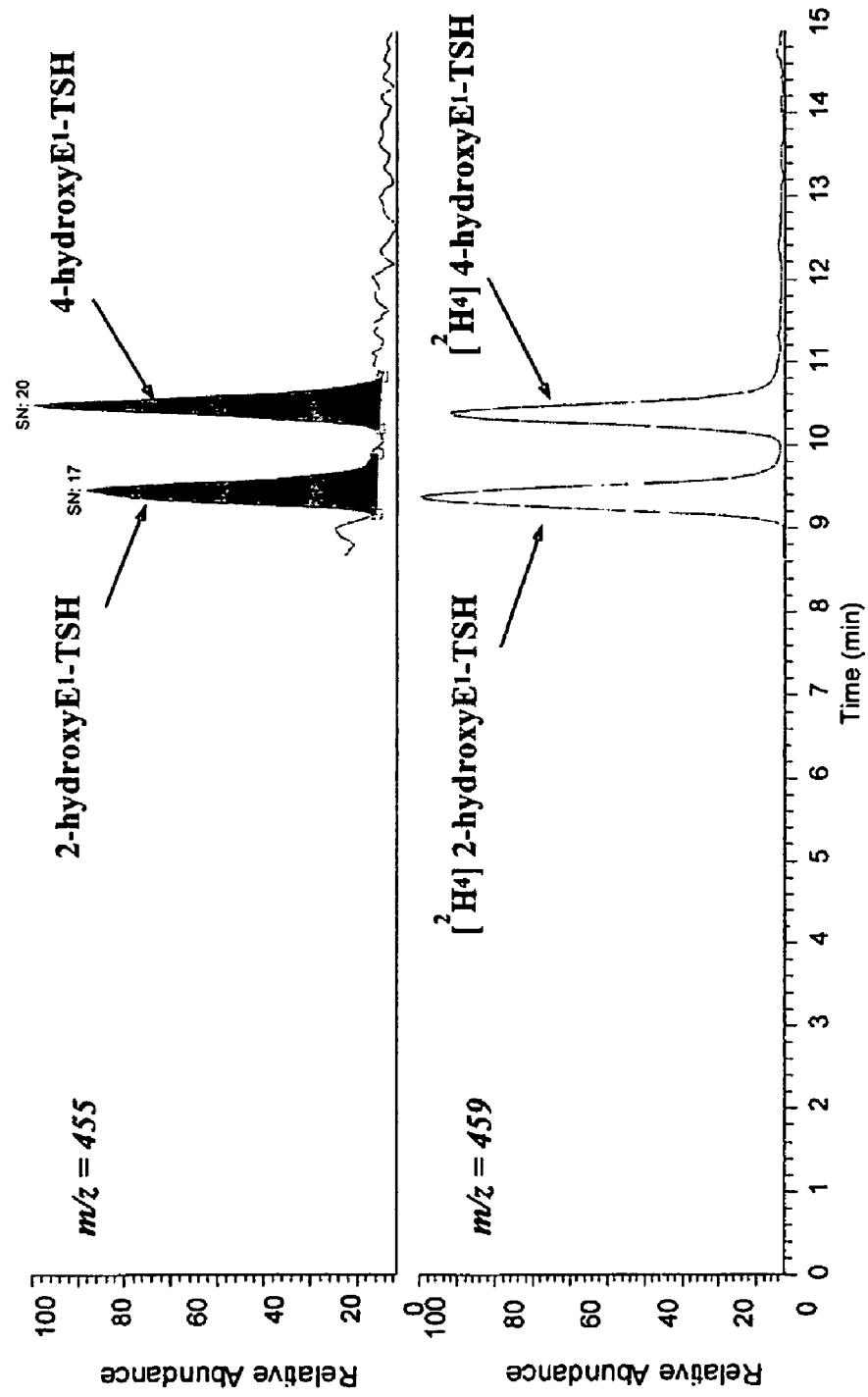
FIGS. 5A-B are HPLC-ESI-MS SIM chromatographic profiles of CE-TSH and d-CE-TSH for a 1-ng working standard (A), and a blank postmenopausal urine sample (B).
Figure 5B:
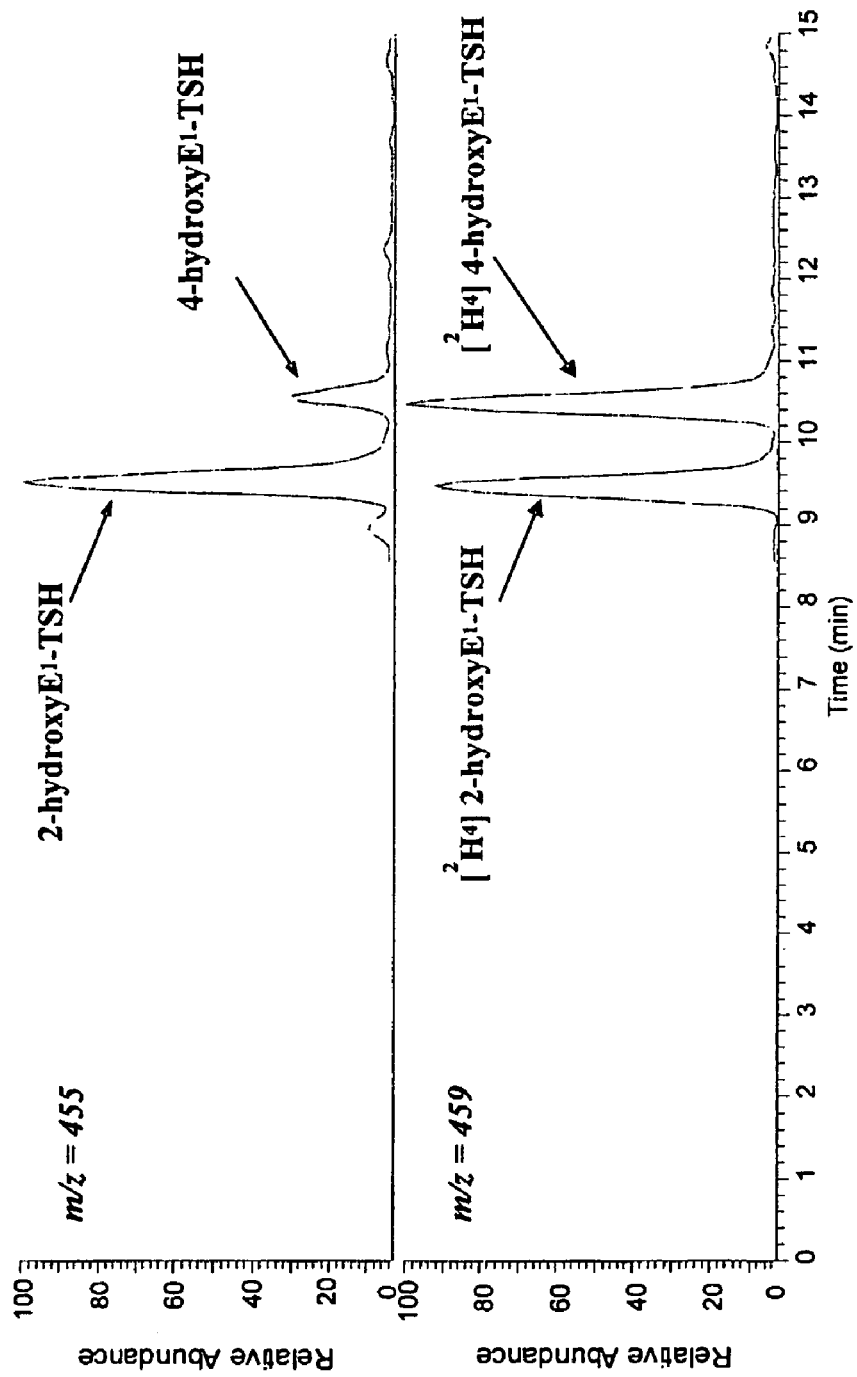

M. Chromatographic SIM Profiles of CE-TSH and d-CE-TSH in Standards and Pooled Human Urine Even though sample preparation in the disclosed method is substantially simplified, compared with the published stable isotope dilution GC-MS method, it is adequate for quantitative analysis of endogenous CE in postmenopausal urine. The HPLC-ESI-MS SIM chromatographic profiles for a 0-ng working standard appropriately gave no signal for the undeuterated CE-TSH (not shown). Analyses of a 1-ng working standard, and a blank postmenopausal urine sample are shown, respectively, in FIGS. 5A and B. Using a simple methanol-water reverse phase HPLC linear gradient, 2-hydroxyE$_1$-TSH and 4-hydroxyE$_1$-TSH were eluted from the C$_{18}$ column in about 9.5 and 10.6 min, respectively, with symmetrical peak shapes. CE-TSH was readily detected and quantified, with no interference, even at the low endogenous levels in postmenopausal urine (FIG. 5B).

N. Standard Curve and Limit of Quantitation

Figure 6:
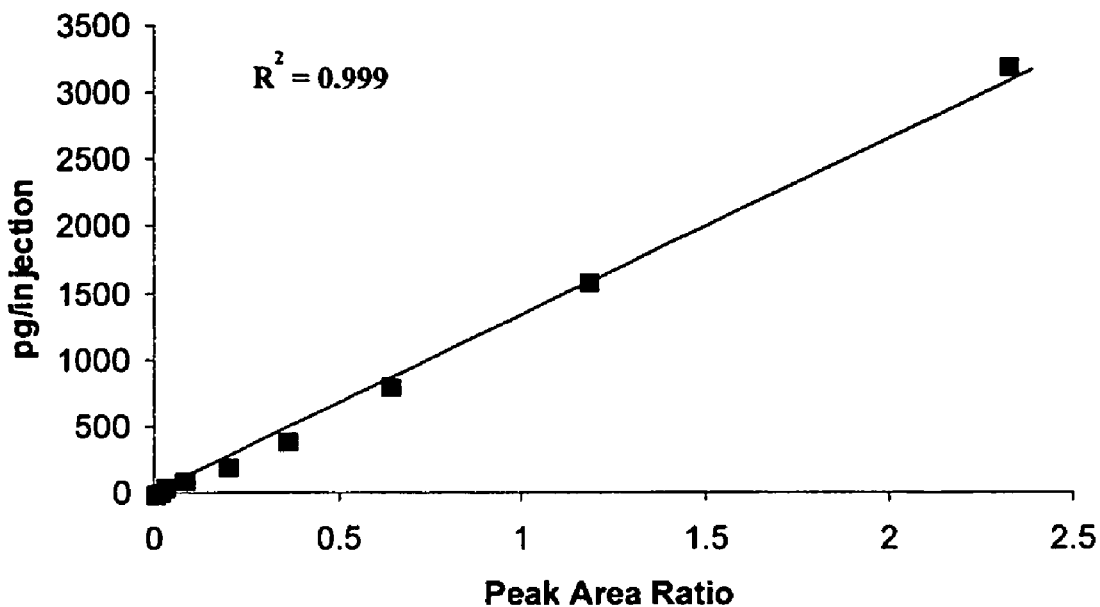
FIGS. 6A-B are graphs showing standard curves for determination of CE in urine.
Figure 6:
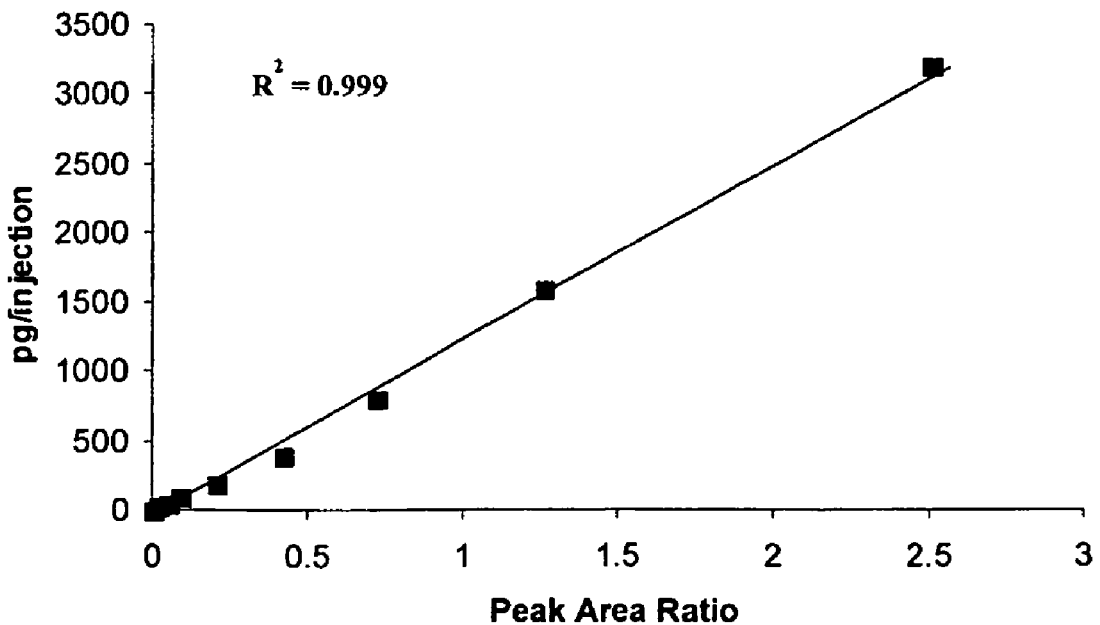

Standard curves for CE were linear over a 100-fold calibration range (0.5-64 ng CE/sample) with correlation coefficients for the linear regression curves typically 0.999 (FIGS. 6A-B). Replicate (n=6) injections of a 1-ng working standard, representing 50 pg on column, resulted in Relative Standard Deviations (R.S.D.) of SIM peak area ratios for 2-hydroxyE$_1$-TSH/[$^2$H$_4$] 2-hydroxyE$_1$-TSH and 4-hydroxyE$_1$-TSH/[$^2$H$_4$] 4-hydroxyE$_1$-TSH of 1.0 and 1.6%, respectively. The Signal to Noise (S/N) ratios obtained for the 1-ng working standard, representing 50 pg on column, were typically greater than 15 (FIG. 5A), which provides an adequate lower limit of quantitation for endogenous CE analyses in urine from postmenopausal women.

O. Absolute Recovery of CE after Hydrolysis and Extraction Procedure

The absolute recovery of CE after the hydrolysis and extraction procedure was determined by comparing SIM chromatographic peak area ratios of CE-TSH/d-CE-TSH in pooled urine from postmenopausal women that had been spiked with d-CE before and after the hydrolysis and extraction procedure. Mean absolute recoveries were 82.4±2.9% and 81.5±2.5%, respectively, for 2-hydroxyE$_1$ and 4-hydroxyE$_1$.

P. Accuracy and Precision of the Urinary CE Analysis

Accuracy, intra and inter batch precision data for the stable isotope dilution HPLC-ESI-MS SIM analysis of human urine samples are presented in Tables 1 and 2 below. The analysis of six 10-ml aliquots of the pooled postmenopausal urine generated a mean concentration for endogenous 2-hydroxyE$_1$ and 4-hydroxyE$_1$ of 9.64 ng/10 ml and 1.40 ng/10 ml, respectively (Table 1). Subtraction of these baseline values from the mean concentrations of six identical postmenopausal urine aliquots to which 8 ng or 30 ng of CE had been added led to the estimates of accuracy, which was 98.76 and 97.06% for 2-hydroxyE$_1$ and 98.01 and 98.99% for 4-hydroxyE$_1$, respectively (Table 1). The intra batch precision, as estimated by the R.S.D. from 6 replicate analyses at each level, ranged from 1.64 to 3.25% for 2-hydroxyE$_1$ and 1.05 to 4.73% for 4-hydroxyE$_1$, respectively (Table 1).

Q. Application to Pre- and Postmenopausal Urine Samples

Figure 7:
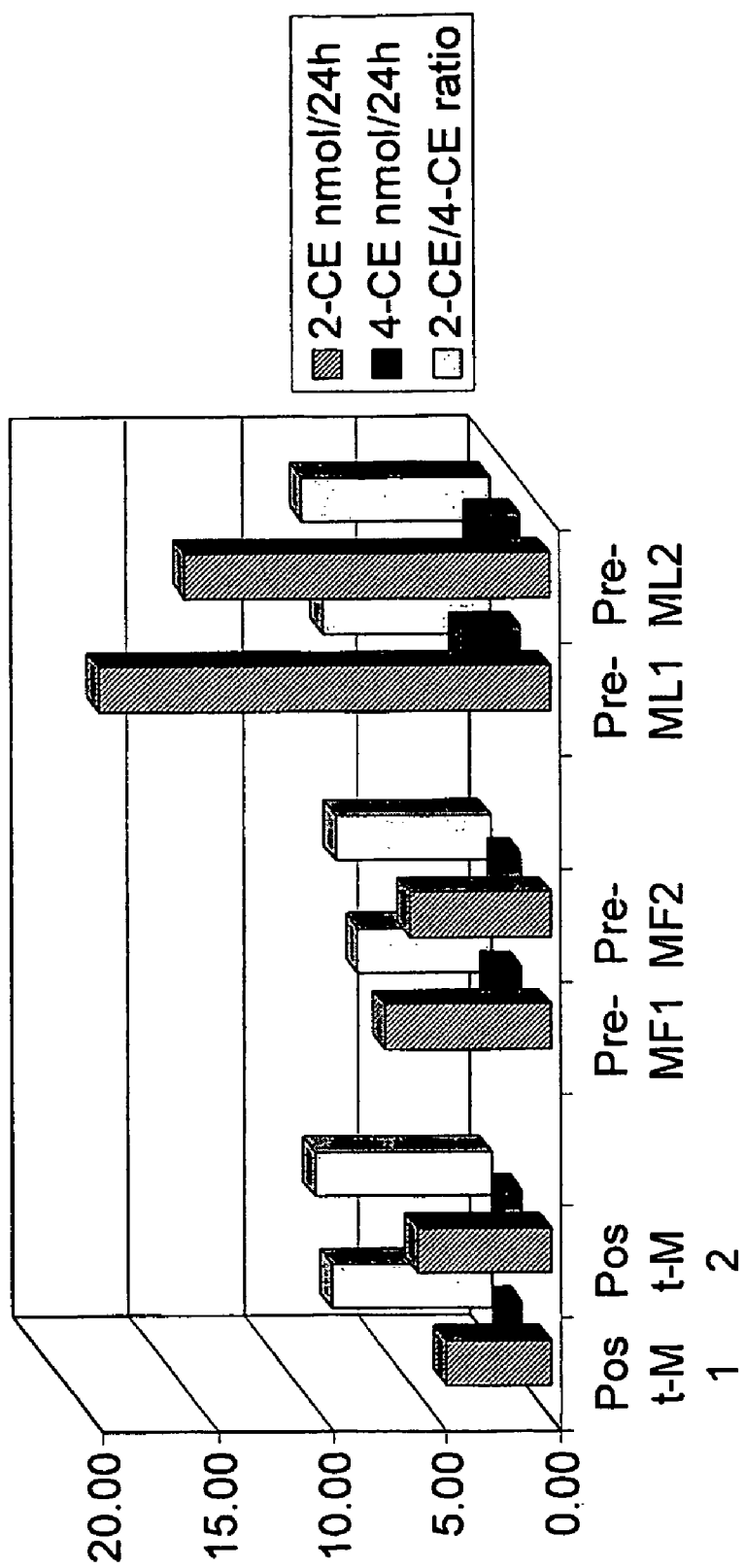
FIG. 7 is a bar graph showing the urinary endogenous CE excretion in post- and pre-menopausal women as determined by the disclosed methods.
Figure 8A:
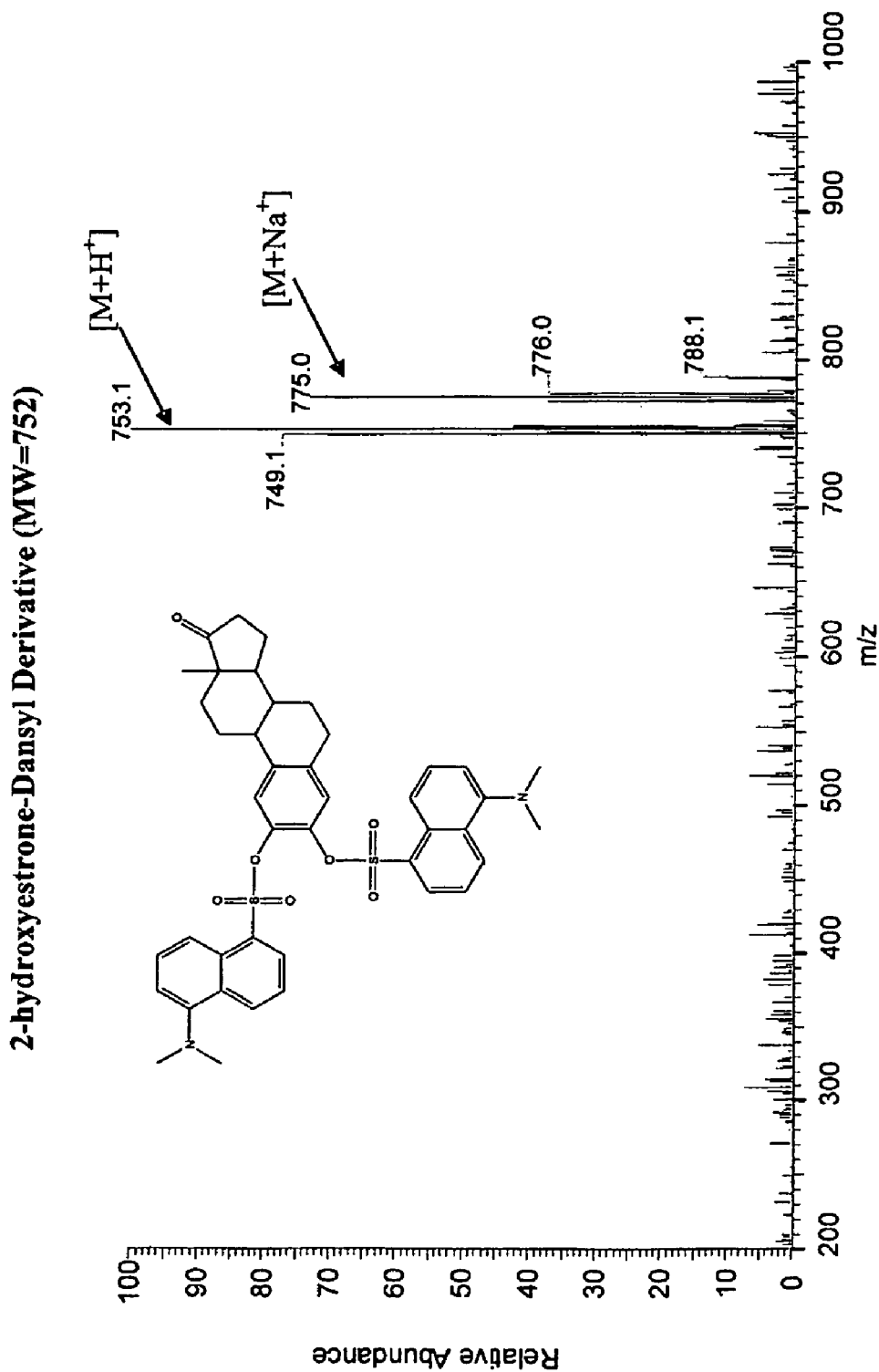
FIG. 8 shows ESI mass spectra for the dansyl derivatives of 2-hydroxyestrone (FIG. 8A), 2-hydroxyestrone-TSH (FIG. 8B); 4-hydroxyestrone (FIG. 8C); and 4-hydroxyestrone-TSH (FIG. 8D).
Figure 8B:
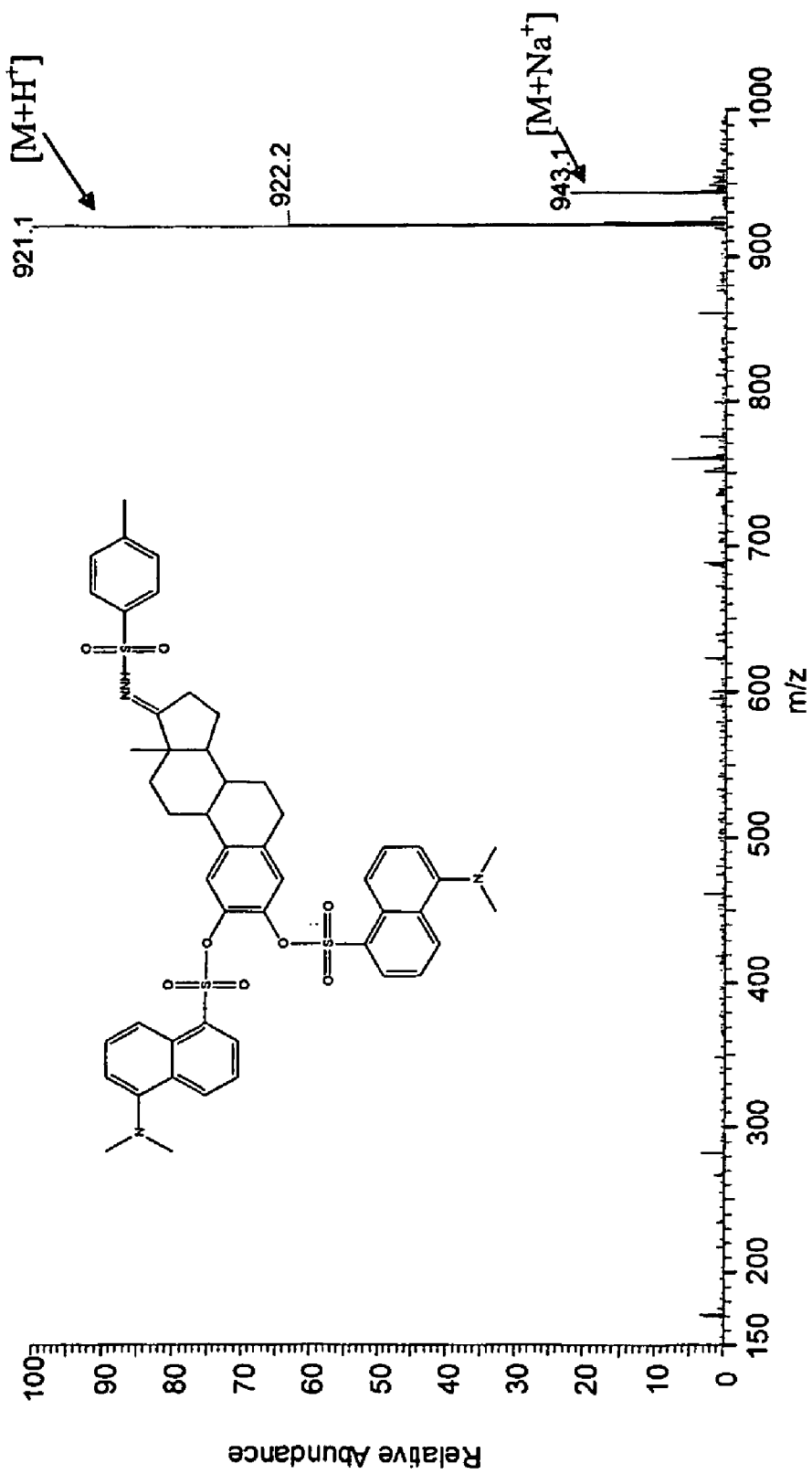
Figure 8C:
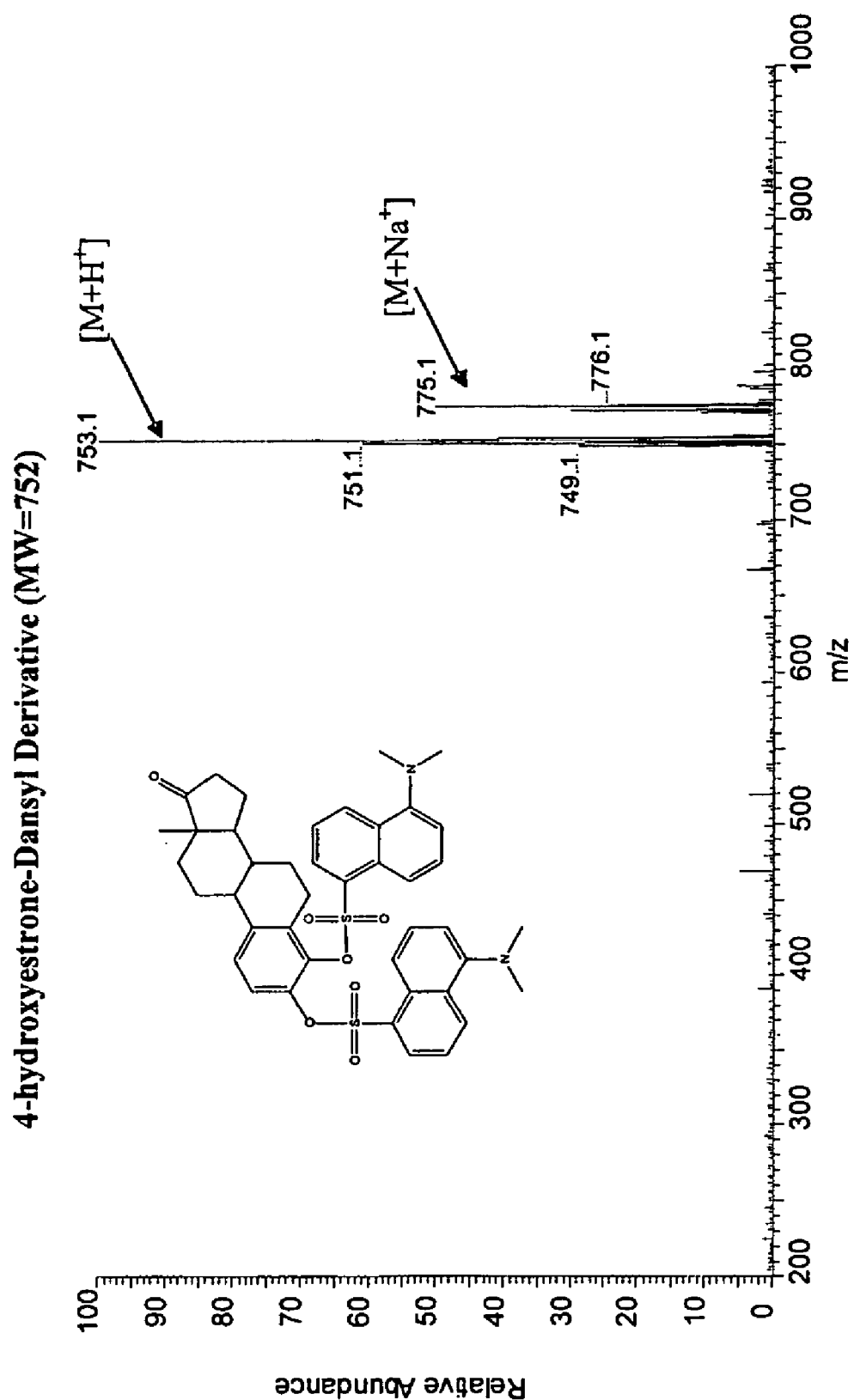
Figure 8D:
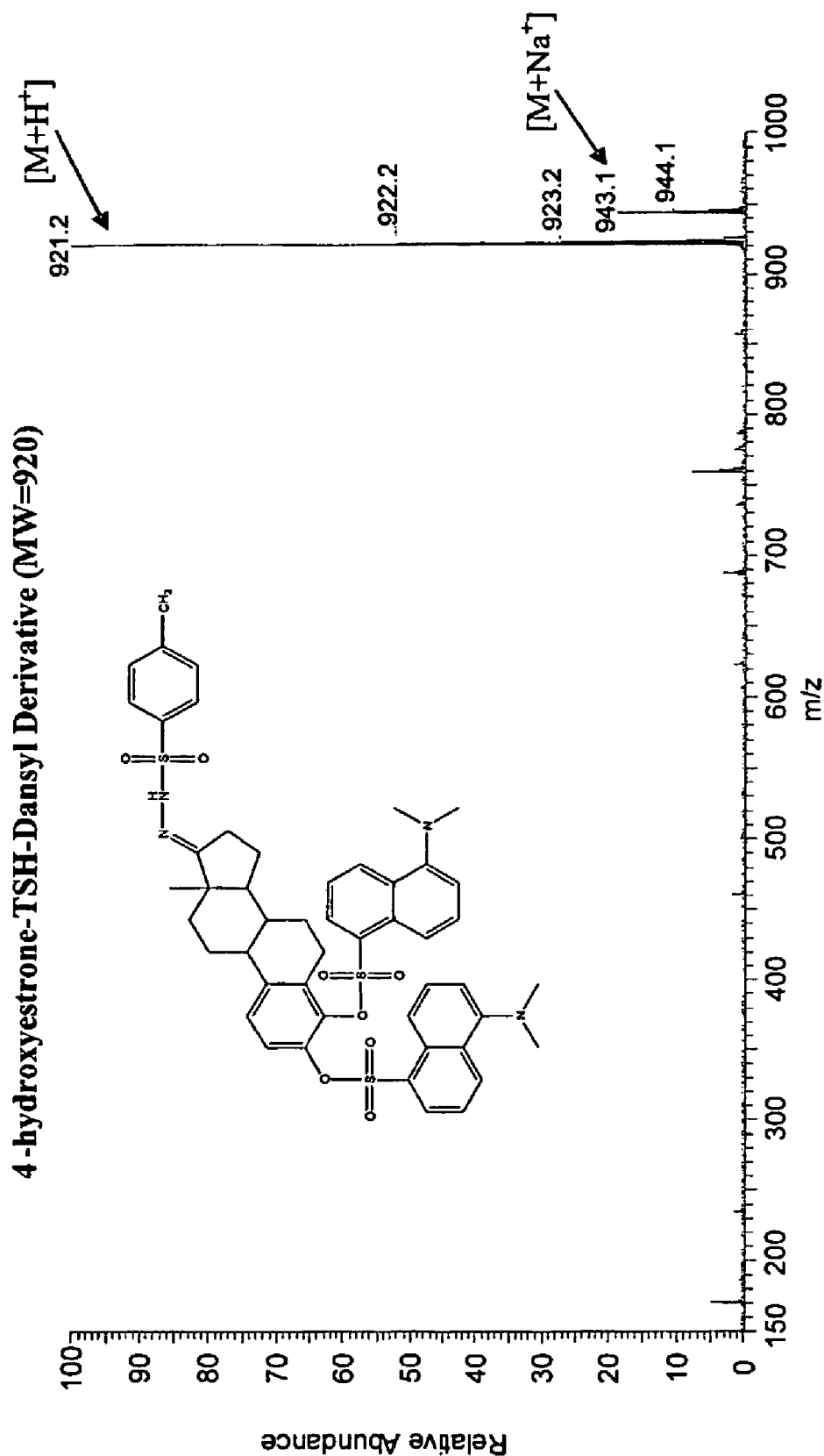
Figure 9A:
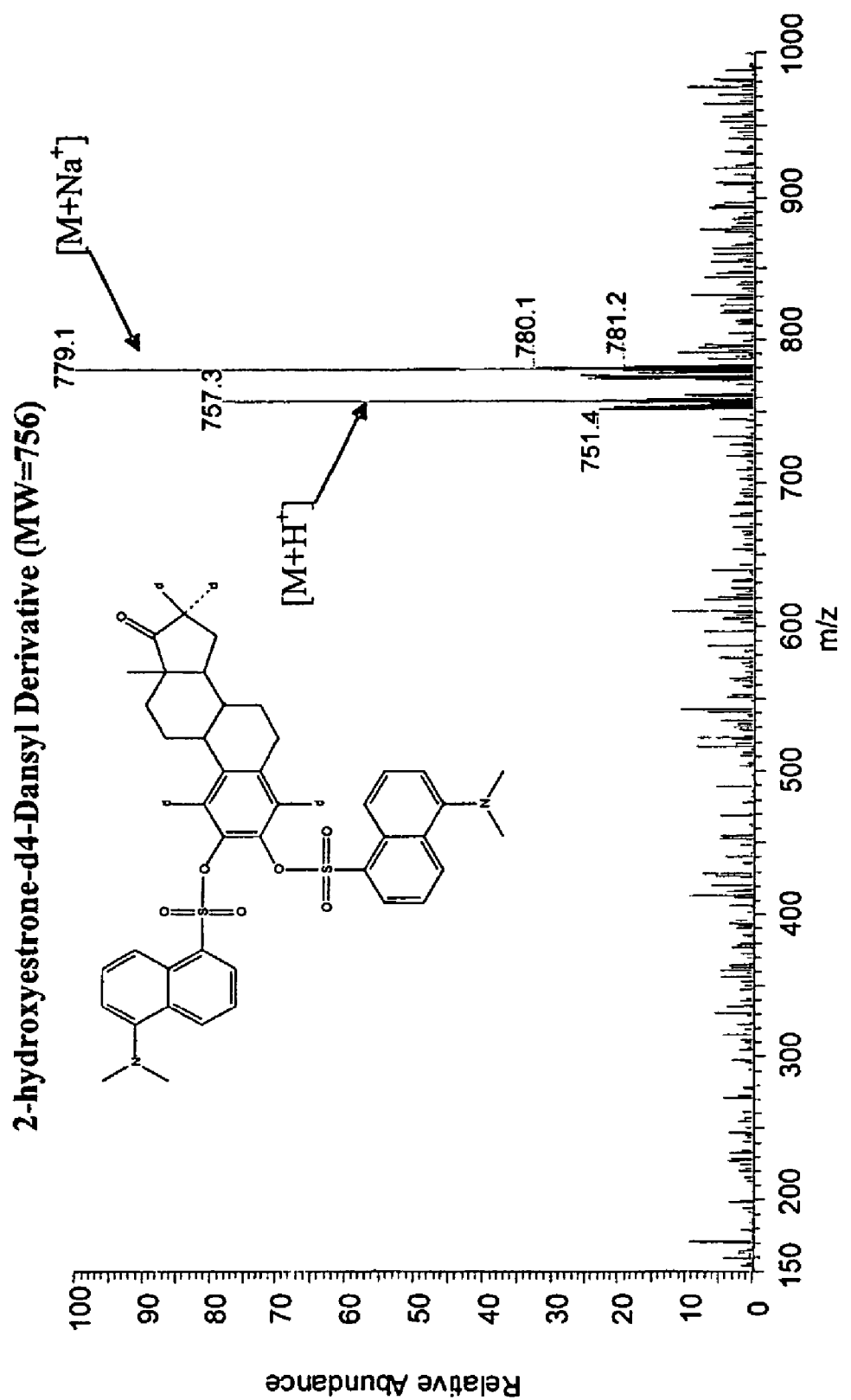
FIG. 9 shows ESI mass spectra for the dansyl derivatives of 2-hydroxyestrone-d4 (FIG. 9A); 4-hydroxyestrone-d4 (FIG. 9B); 2-hydroxyestradiol (FIG. 9C); 4-hydroxyestradiol (FIG. 9D); 2-hydroxylestradiol (FIG. 9E); and 4-hydroxylestradiol (FIG. 9F).
Figure 9B:
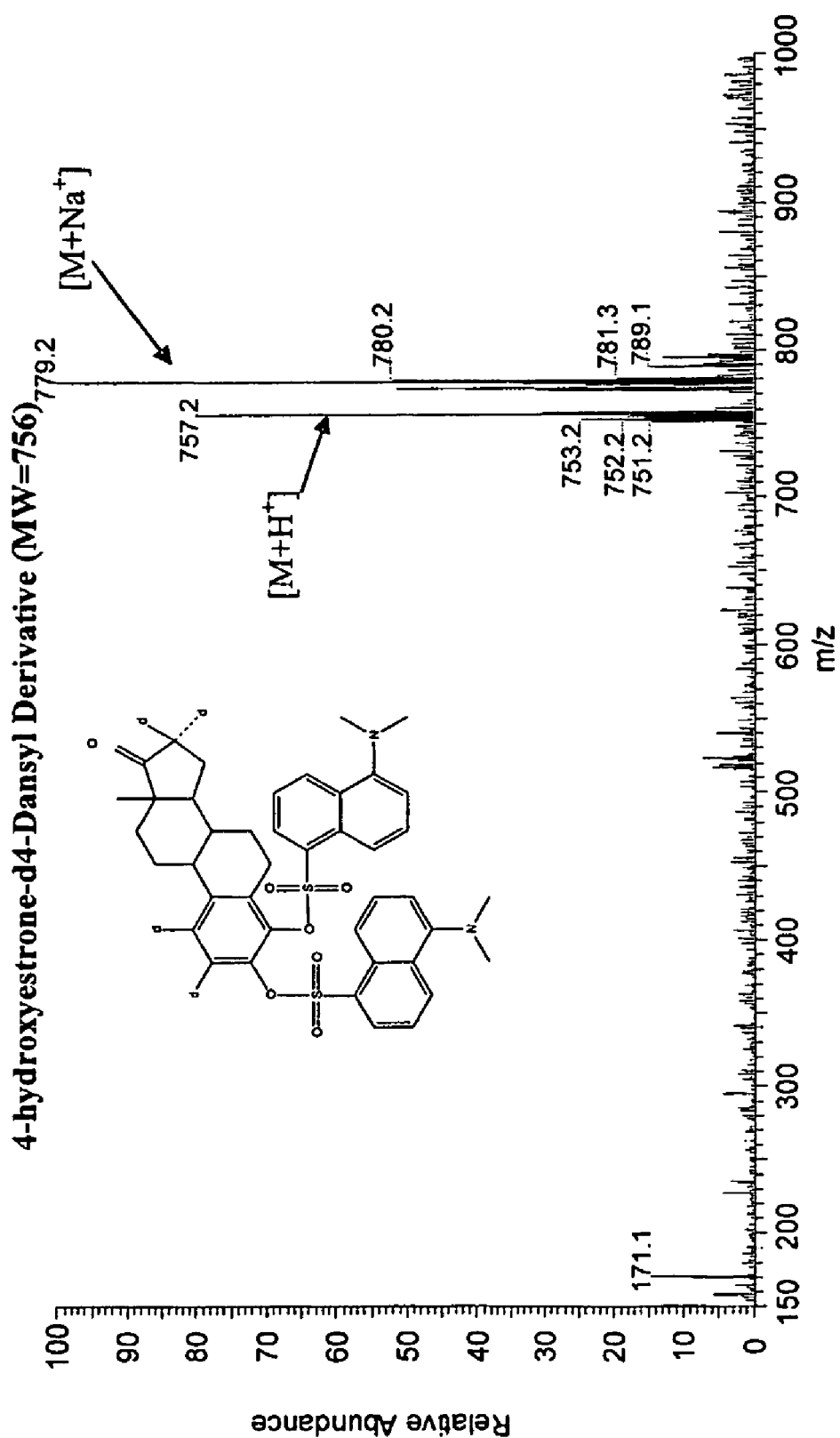
Figure 9C:
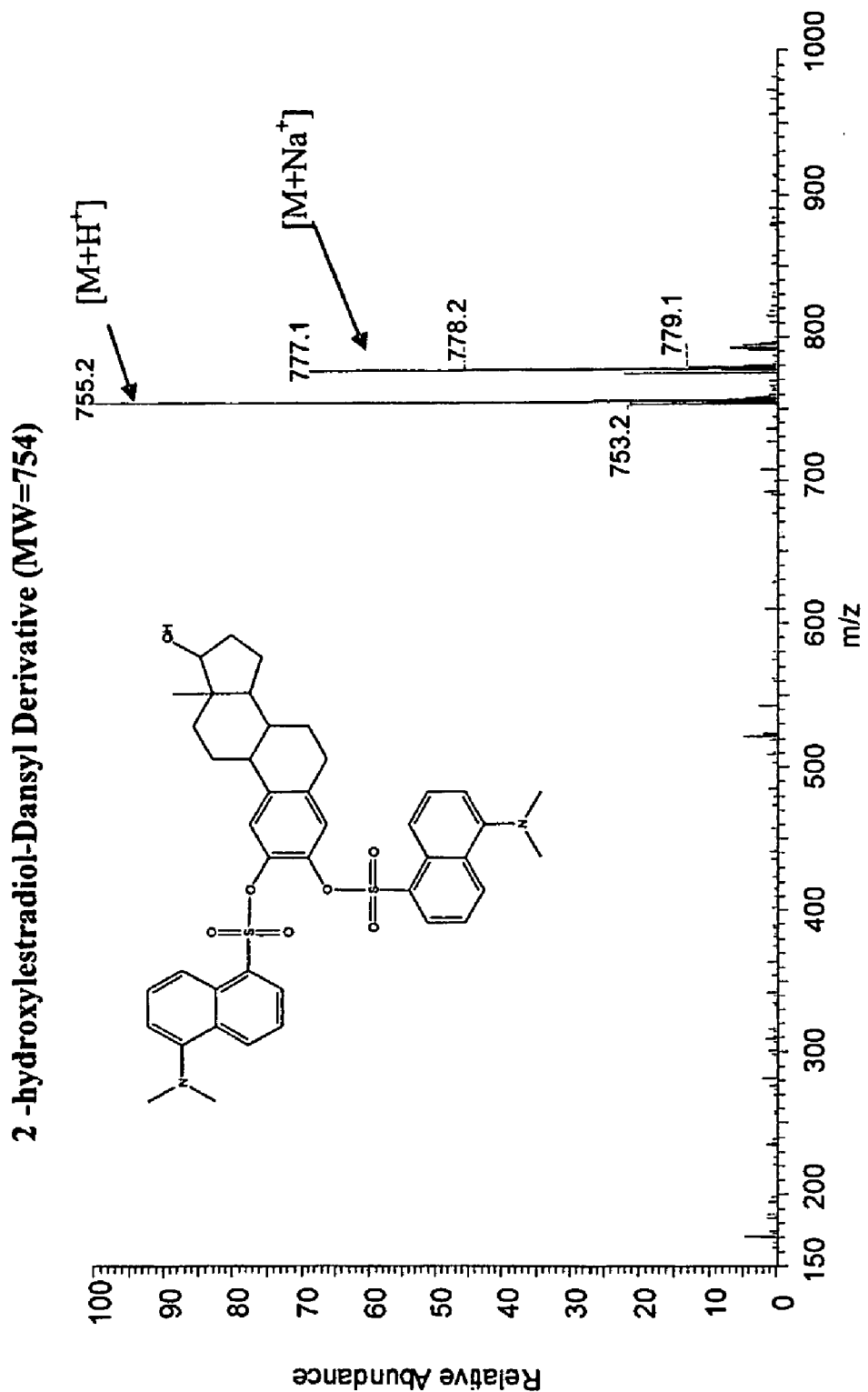
Figure 9D:
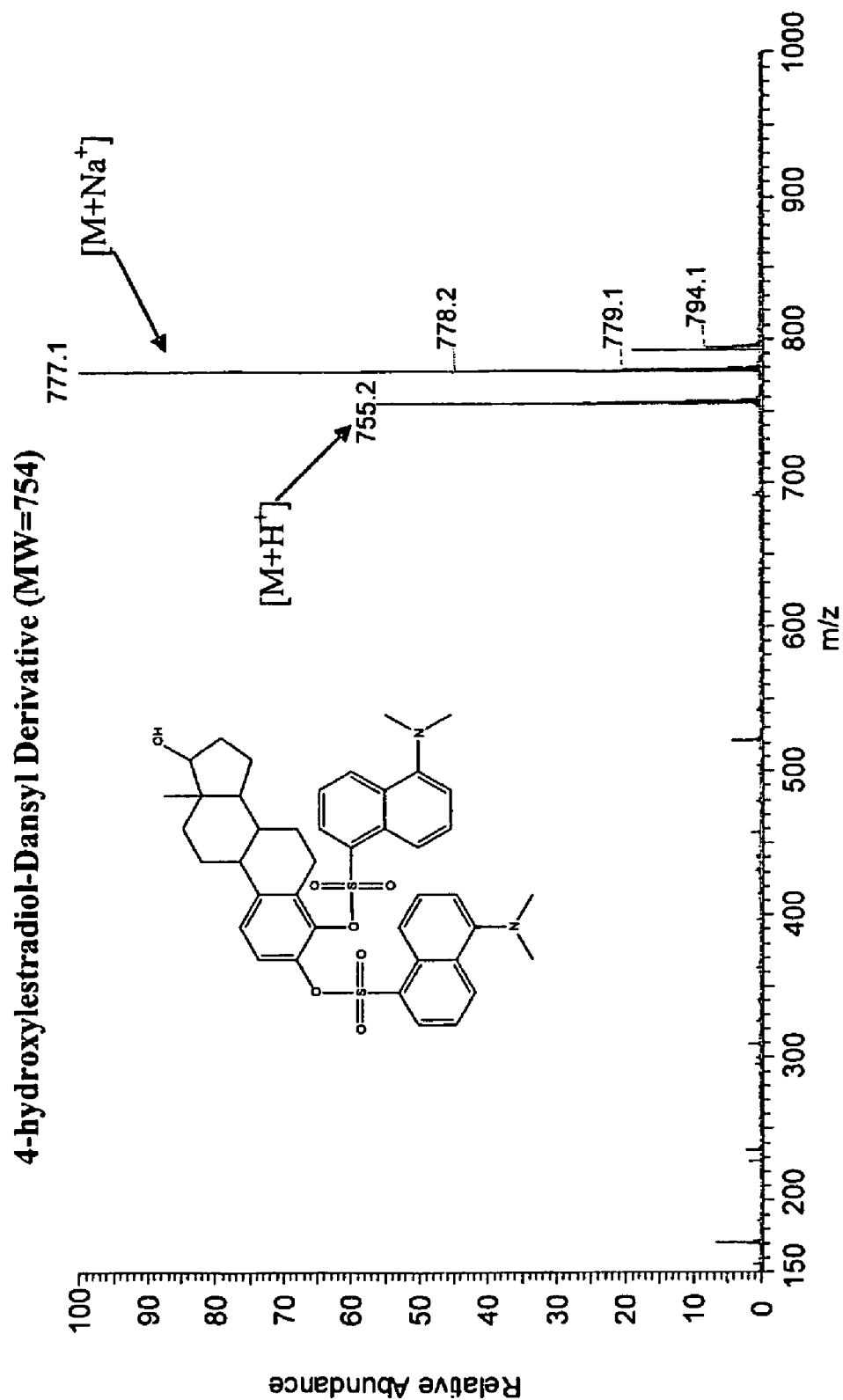
Figure 9E:
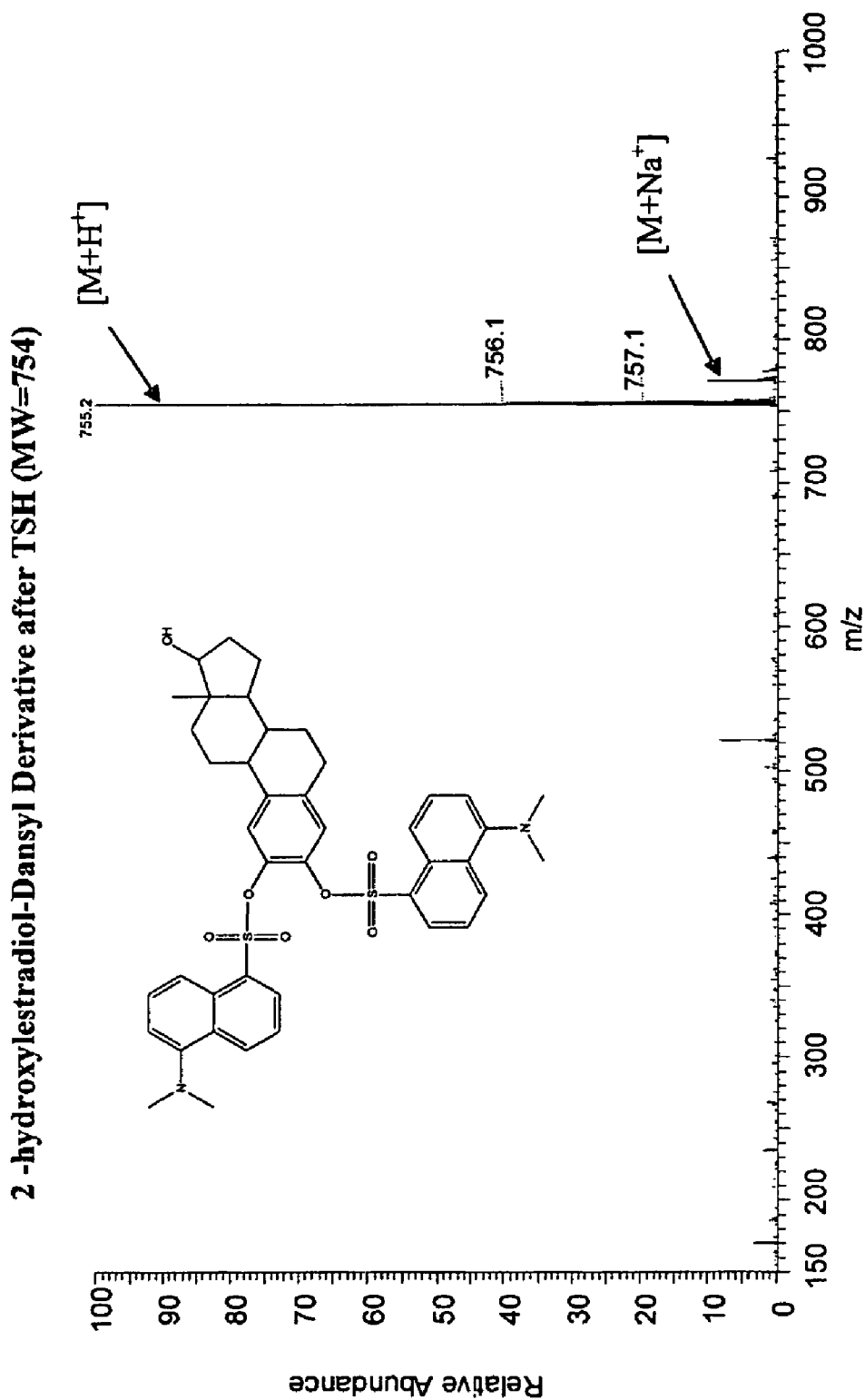
Figure 9F:
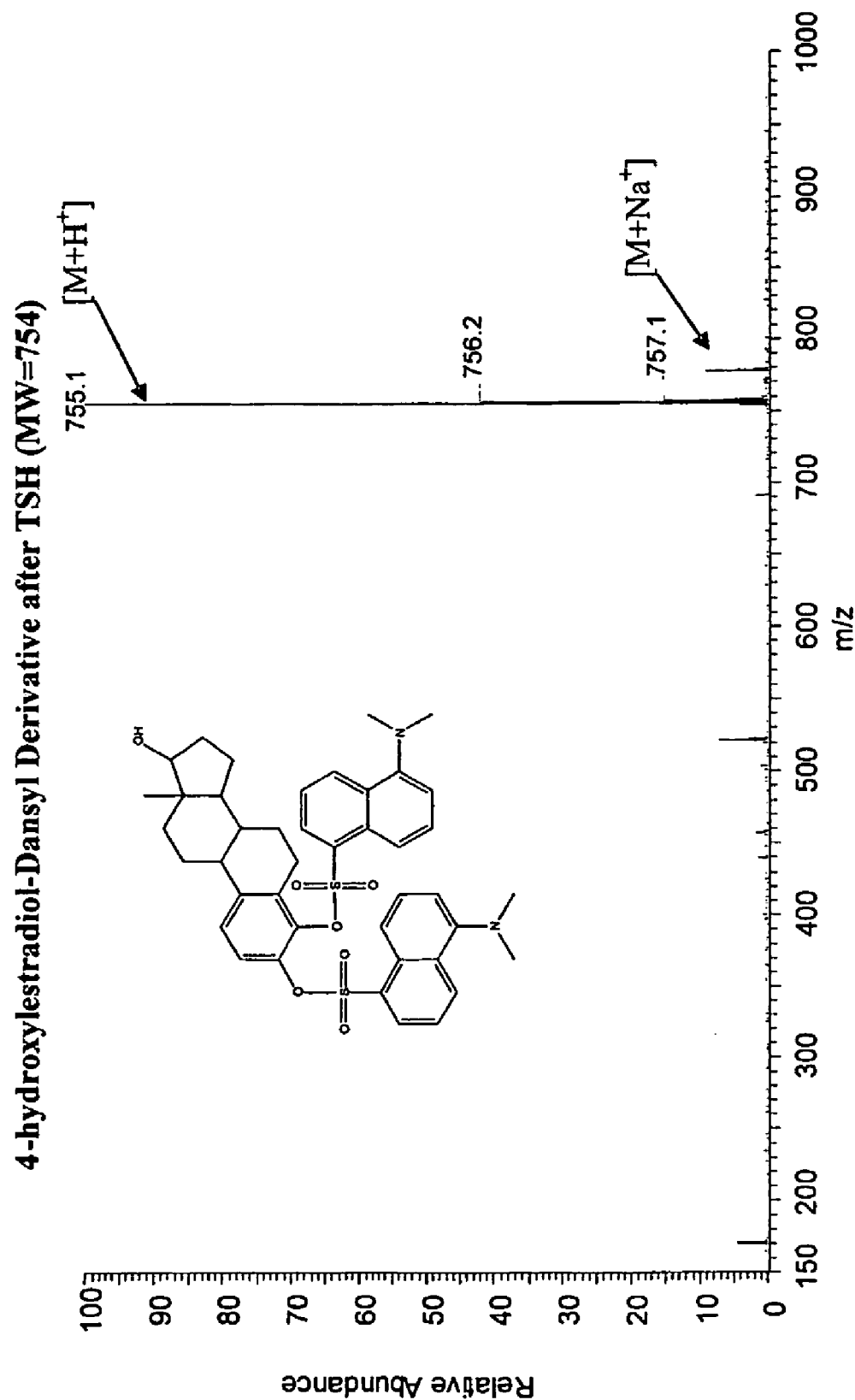

The usefulness of the disclosed method was also demonstrated in the analyses of endogenous CE in the non-pooled urine samples from two postmenopausal women and two premenopausal women during midfollicular and midluteal phases as described above. Duplicate 10-ml aliquots from each 24-h urine sample were hydrolyzed, extracted, derivatized, and analyzed to determine CE concentration. When this information was combined with the associated 24-h urine volume, it provided estimates of 24-h urinary CE excretion (2CE=2-hydroxyE1; 4CE=4-hydroxyE$_1$) in each of the postmenopausal women (Post-M) and premenopausal women during midfollicular (Pre-MF) and midluteal phases (Pre-ML) (FIG. 7). These data correspond with the results of other reported studies (see, for example, Aldercruetz et al., J. Natl. Cancer Inst., 86: 1076, 1994).

The HPLC-ESI-MS method for measuring endogenous CE in human urine described above simplifies sample preparation and increases the throughput of analysis. The disclosed method provides a simple and rapid derivatization step that forms p-toluenesulfonhydrazone derivatives of CE and d-CE. This derivatization step greatly enhances ESI-MS sensitivity as well as HPLC separability of the 2- and 4-hydroxyE$_1$. Standard curves were linear over a 100-fold calibration range (0.5-64 ng CE/sample) with correlation coefficients for the linear regression curves typically 0.999. The lower limit of quantitation for each CE is 1 ng per 10-ml urine sample, with accuracy of 97-99% and overall precision, including the necessary preparation and derivatization steps, of 1-3% for samples prepared concurrently and 2-11% for samples prepared in several batches. This method is useful for measuring

TABLE 1

Accuracy and intra batch precision of urinary CE analyses, including hydrolysis, extraction, and derivatization steps$^a$

|  | Postmenopausal urine | | Postmenopausal urine + 8 ng CE | | Postmenopausal urine + 30 ng CE | |
| --- | --- | --- | --- | --- | --- | --- |
|  | 2-hydroxyE$_1$ | 4-hydroxyE$_1$ | 2-hydroxyE$_1$ | 4-hydroxyE$_1$ | 2-hydroxyE$_1$ | 4-hydroxyE$_1$ |
| Mean (n = 6) | 9.64 | 1.40 | 17.54 | 9.24 | 38.76 | 31.10 |
| SD (n = 6) | 0.31 | 0.07 | 0.29 | 0.18 | 1.15 | 0.33 |
| Accuracy (%) | N/A | N/A | 98.76 | 98.01 | 97.06 | 98.99 |

$^a$The mean is expressed in units of ng/10 mL of urine.

The inter batch precision estimated by the R.S.D. for 4 independent batch analyses of pooled postmenopausal and premenopausal midluteal urine samples were 2.36 and 2.37% for 2-hydroxyE$_1$ and 4.44 and 10.68% for 4-hydroxyE$_1$, respectively (Table 2).

TABLE 2

Inter-batch precision of urinary CE analyses, including hydrolysis, extraction, and derivatization steps$^a$

|  | Postmenopausal urine | | Premenopausal mid-luteal urine | |
| --- | --- | --- | --- | --- |
|  | 2-hydroxyE$_1$ | 4-hydroxyE$_1$ | 2-hydroxyE$_1$ | 4-hydroxyE$_1$ |
| Mean (n = 4) | 9.78 | 1.34 | 32.46 | 3.95 |
| SD (n = 4) | 0.23 | 0.06 | 0.77 | 0.42 |
| Precision (%) | 2.36 | 4.44 | 2.37 | 10.68 |

$^a$The mean is expressed in units of ng/10 ml urine.

the low endogenous levels of 2- and 4-hydroxyE$_1$ in urine from postmenopausal women.

Example 2

Derivatization Agents and Methods

Examples of sulfonhydrazide compounds useful for forming ESI-MS detectable derivatives of carbonyl-containing compounds have the structure

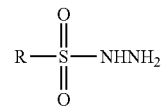

where R is selected from the group consisting of alkyl, substituted alkyl, aryl, and substituted aryl. Alkyl groups includes C1-C18 straight and branched chain alkyl groups (for example C1-C10 or C1-C5 groups). Substituted alkyl includes alkyl groups in which one or more hydrogens are substituted with halogen (F, Cl, Br, I), amino groups or hydroxyl groups. Aryl includes phenyl, napthyl, and anthranyl groups. Substituted aryl includes phenyl, napthyl, and anthranyl groups where one or more hydrogens are substituted with C1-C5 alkyl, C1-C4 alkoxy, halogen, amino, nitro, hydroxyl, carbonyl, nitroso, cyano, and sulfonyl groups, and combinations thereof.

In some embodiments, the sulfonhydrazide compound has the structure

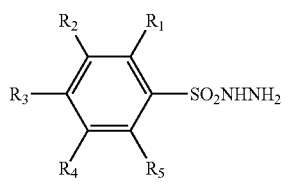

wherein $R_1$-$R_5$ are independently selected from the group consisting of hydrogen, $C_1$-$C_5$ alkyl, C1-C4 alkoxy, halogen, amino, nitro, hydroxyl, carbonyl, nitroso, cyano, and sulfonyl, and combinations thereof. C1-C5 alkyl includes methyl, ethyl, propyl, isopropyl, n-butyl, sec-butyl, isobutyl, tert-butyl, and neopentyl groups. C1-C4 alkoxy includes, methoxy, ethoxy, propoxy, isopropoxy, n-butoxy, sec-butoxy, isobutoxy, and tert-butoxy groups. One example of a sulfonhydrazide compound having this structure is p-toluenesulfonhydrazide, wherein $R_3$ is methyl and $R_1$, $R_2$, $R_4$, and $R_5$ are hydrogen. Another example is benzenesulfonyl hydrazide where $R_1$-$R_5$ are all hydrogen. Both p-toluenesulfonhydrazide and benzenesulfony hydrazide are available from Aldrich (Milwaukee, Wis.), as are 2,4,6-triisopropylbenzenesulfonyl hydrazide, 2,4,6-trimethylbensenesulfonyl hydrazide, 4-methoxybenzenesulfonyl hydrazide, and 4-amino-2-nitrobenzenesulfonyl hydrazide. Other sulfonhydrazides may be synthesized by reacting a sulfonyl halide (such as sulfonyl chloride) compound with hydrazine, an amine (see, Streitwieser and Heathcock, "Introduction to Organic Chemistry," Macmillan Publishing Co., Inc., 1976, pages 789-790). For example methanesulfonyl chloride may be reacted with hydrazine to form methanesulfonyl hydrazide. Over 150 sulfonyl chloride compounds are available from Aldrich (Milwaukee, Wis.). Others may be synthesized from sulfonic acid compounds by reaction with $PCl_5$.

Sulfonhydrazide compounds may be reacted with carbonyl-containing compounds by combining the two compounds in a solvent that will dissolve both but does not itself react with the sulfonhydrazide compound (for example, acetone would be a bad choice). Methanol is a good solvent in which to react sulfonhydrazide compounds with carbonyl compounds, such as ketosteroids, because it is a good solvent for both polar and non-polar solutes and it will not react with the sulfonhydrazide compound. Once combined the reaction mixture may be heated to accelerate the reaction, for example, to between 30° C. and 65° C. (reflux) when methanol is the solvent. A general procedure for forming p-toluenesulfonhydrazone derivatives of carbonyl compounds in methanol may be found in Banwell et al., *J. Chem. Soc. Perkin Trans.*, 1: 945, 1993. In this method, the carbonyl containing compound is combined with the sulfonhydrazide compound in methanol that is initially warmed to 50° C. The reaction is then left to sit at room temperature for 12-24 h. Another example is found in Banks et al., *J. Am. Chem. Soc.*, 115:2473-2477, 1993, where ethanol is substituted for methanol and the reaction mixture containing the sulfonhydrazide compound and the carbonyl-containing compound is refluxed (78° C.) for about 4 hours. The time of reaction will depend upon the particular carbonyl-containing compound and the temperature (such as between about 25° C. and 100° C.) of the reaction mixture, but may vary from 15 minutes to about 2 days, with 30 minutes to a few hours being typical.

For TSH derivatization of estrogens, a series of TSH concentrations, reaction times, temperature of reaction and addition of an acid were investigated to determine appropriate reaction conditions for derivatization. Estrogen samples were incubated at 60° C. for 0.5, 1, 1.5 or 2 hours in 200 μL of 0.5 mg TSH/mL 100% methanol, 1 mg TSH/mL 100% methanol or 2 mg TSH/mL 100% methanol. Improved derivatization was obtained using the 2 mg TSH/mL 100% methanol solution, which showed no significant difference between the incubation periods. Estrogen samples were also incubated with 2 mg TSH/mL solutions in methanol that also contained 0.05 M or 0.10 M acetic acid. These samples showed improved intensity of the protonated molecular ions. Different temperatures (45, 50, 55 and 60° C.) were tried while holding the TSH concentration and time constant, and revealed that derivatization was more effective at 55° C. and 60° C. The TSH-estrogen adducts were also observed to be quite stable. When incubation mixtures were left at room temperature for periods of 24-72 hours, little degradation or decomposition was observed.

Example 3

Ketosteroids

As used herein, ketosteroids include steroids having at least one carbonyl group. Groups of steroids that include numbers of ketosteroids are androgens, corticoids, estrogens, sterols, vitamin D metabolites, phytosteroids, neurosteroids and bile acids (see, for example, Shimada et al., *J. Chromatogr. A*, 935: 141-172, 2001, for a discussion of the many types of steroids and many particular examples of ketosteroids). The basic steroid molecular skeleton consists of four rings of carbon atoms, perhydro-1,2-cyclopentenophenanthrene. Many steroids fall within six broad groups according to the number of carbon atoms in the 4-ring skeleton and in side chains, namely, gonanes (C17), estranes (C18), androstanes (C19), pregnanes (C21), cholanes (C24), and cholestanes (C27). Any of these skeletons bearing a carbonyl group is also a ketosteroid. Particular examples of ketosteroids include the carbonyl-bearing testosterones, testosterone esters, androsterones, norandrosterones, noretiocholanolones, cortisols, cortisones, aldosterones, corticosterones, tetrahydrocortisones, etiocholanolones pregnenolones, protesterones, estrones, gestrinones, oxosterols, guaicol estrogens, and metabolites of these compounds. Ketosteroids may be naturally occurring or synthetic, making the methods of the disclosure applicable to metabolic studies as well as for detecting abuse of performance enhancing steroids.

Example 4

HPLC

The principles of chromatography, such as liquid chromatography, for example high-performance liquid chromatography and its more sensitive variants, nano-LC and capillary HPLC, are described in depth in several excellent textbooks including Scott, *Techniques and Practices of Chromatography*, Marcel Dekker 1995; Meyer, *Practical High-performance Liquid Chromatography*, 2nd Ed., Wiley, New York, 1994; McMaster, "*HPLC: A Practical User's Guide*, VCH Publishers, Inc., 1994; and Krustulovic and Brown, *Reversed-Phase HPLC: Theory, Practice and Biomedical Applications*, Wiley-Interscience, New York, 1982. Nano-LC is also described in a review article by Guetens et al. (Guetens et al., *J. Chromatogr. B*, 739: 139-150, 2000). A discussion of coupled liquid chromatography and mass spectrometry is found in Niessen and van der Greef, *Liquid Chromatography-Mass Spectrometry*, Marcel Dekker, Inc., 1992.

Briefly, HPLC is a form of liquid chromatography, meaning the mobile phase is a liquid. The stationary phase used in HPLC is typically a solid, more typically a derivatized solid having groups that impart a hydrophilic or hydrophobic character to the solid. For example, silica gel is often used as the base solid and it is derivatized to alter its normally hydrophobic characteristics. Normal phase HPLC refers to using a non-polar mobile phase and a polar stationary phase. Reverse phase HPLC refers to a polar mobile phase and a non-polar stationary phase. Reverse phase HPLC is convenient because polar solvents such as water, methanol, and ethanol may be used and these solvents are easily and safely handled and disposed. Furthermore, reverse phase conditions improve ESI efficiency.

Typical reverse phase mobile phase solvents include polar protic solvents such as water, methanol, ethanol, and sometimes other alcohols and polar aprotic solvents such as dimethylformamide and acetonitrile. Of these, methanol and water are particularly convenient to use, especially since they are miscible in all proportions with each other. When a single solvent system (either a single solvent or a mixture of solvents) is used the chromatography is termed isocratic. When the composition of the mobile phase solvent is changed during a chromatographic run it is termed a gradient elution. For reverse phase HPLC, a gradient begins with the more polar solvent mixture and then progressively is changed to a more non-polar solvent system. For example, a reverse phase gradient elution may begin with a 20:80 methanol/water mixture and change to an 80:20 methanol/water mixture during the course of a chromatographic run. Other examples of methanol/water mixture gradients include beginning with a 25:75 methanol/water mixture and changing to 75:25 methanol/water during the chromatographic run or beginning with a 40:60 methanol/water solvent and changing to a 60:40 methanol/water mixture. Formic acid may also be added to the solvent in an amount from 0.05% to 1%, such as from 0.05% to 0.2%, to assist in positive ion mode ESI of the HPLC effluent.

A convenient isocratic solvent system for separation of p-toluenesulfonhydrazide derivatized catechol estrogens is a 60:40 methanol/water mixture. Such a solvent system has an espsilon value (solvent strength parameter) of about 51. One of ordinary skill in the art of chromatography will recognize that other solvent systems of similar epsilon value can be chosen to accomplish the separation. For example, a 50:50 acetonitrile/water mixture has an epsilon value of 50 and may be chosen as an alternative solvent system. Similarly, equivalents for other methanol/water solvents that are better suited for particular ketosteroid separations may be chosen on the basis of epsilon values. Mixtures of solvents may be mixed beforehand or be mixed during a chromatographic run in varying proportions in what is called a gradient elution. In general, appropriate solvent systems and gradients for reverse phase HPLC will have an epsilon value from 30 to 80, for example, from 40 to 70, such as from 45 to 55. Examples of solvents that may be used to provide an epsilon values from 30 to 80 include water, methanol, ethanol, and acetonitrile.

As stated above, reverse phase HPLC is better suited to ESI conditions than normal phase HPLC. For reverse phase HPLC, the non-polar stationary phase may be a C8 or a C18 derivatized column or an embedded polar/non-polar column such as an amine/C18 or C8 column. In the embedded column, polar groups close to the surface of the solid stationary phase support are interspersed with non-polar C8 or C18 groups. Many types of non-polar columns for reverse phase HPLC are available, for example, from Alltech Associates, Inc. (Deerfield, Ill.).

In some instances it may be desirable to utilize a nano-LC (capillary HPLC) technique to increase sensitivity of the disclosed methods. Nano LC is often combined with online mass spectrometry using micro- or nano-ion spray (variants of ESI). Nano-LC columns are available in a variety of sizes and lengths. For example, a typical column might have an inner diameter of 75 μm and a length of between 5 and 25 cm. A typical nano-LC packing is C18, with a 5 μm particle size, making it especially suitable for separations of ketosteroids according to the disclosed methods. Nano-LC equipment is available, for example, from LC Packings (San Francisco, Calif.).

Example 5

Derivatization for ESI

It is also possible to use sulfonhydrazide compounds to increase the ionization efficiency of carbonyl-containing compounds under positive ion mode ESI conditions and thereby lower the limit of detection of the compound by ESI-MS. In this embodiment, a sulfonhydrazide compound is added to a liquid sample containing a carbonyl-containing compound and allowed to react to form a sulfonhydrazone derivative of the carbonyl-containing compound. The sample is then injected in liquid form (with or without further purification) into an ESI-MS device for measurement (see for example, Fenn et al., "Electrospray Ionization-Principles and Practice," *Mass Spectrom. Rev.,* 9: 37-70, 1990).

Example 6

Mass Spectrometers

An API interface (such as an ESI interface) may be used to introduce a liquid sample into any type of mass spectrometer in API-MS. Examples of the types of mass spectrometers that may be used include sector instruments, quadrupole instruments, ion-cyclotron resonance instruments, time-of-flight instruments, and tandem mass spectrometers. A particularly useful type of tandem mass spectrometer for ESI ionized samples is an instrument having a collision cell, such as a low-energy or high-energy collision cell, placed between the mass selecting regions of the spectrometer. Since ESI typically creates ions from molecules without breaking them apart, it is advantageous to break the ions apart into fragment ions in a collision cell. The fragmentation pattern created in the collision cell is detected by a second mass selective device and may be used for identification of the analyte.

Example 7

Comparison of Sulfonhydrazide Derivatization with Other Derivatization Schemes To demonstrate the exceptional signal enhancing ability of sulfonhydrazide derivatization for API-MS and the advantageous HPLC properties of p-toluenesulfonhydrazones derived from ketosteroids, other types of derivatives were prepared and tested. Methoxyamine and ethoxyamine derivatization of the carbonyl group of catechol estrogens produced no detectable signal in either ESI or Atmospheric Pressure Chemical Ionization (ACPI) experiments. Carboxymethoxylamine (CMA) formed the derivatized product and it was detectable in both ESI and ACPI experiments. However, CMA derivatives were not stable during either ESI or ACPI and decomposed, making quantification more difficult. Girard's Reagent P and T (quaternary ammonium hydrazine compounds with a permanent positive charge) derivatives showed improved signal for ESI, but they adversely affected the HPLC separation of catechol estrogens. 6-Ethoxy-2-benzothiazolesulfonamide, N'-(2-thiazolyl)sulfanilamide, sulfisomididine, and sulfadiazine were also tried as derivatization agents, but no signal was observed in either ESI or ACPI. Sulfonyhydrazide derivatization, by comparison, showed the best enhancement of the ESI signal, and p-toluenesulfonylhydrazide derivatization in particular was most effective for improving the chromatographic behavior of the ketosteroid catechol estrogens.

Example 8

Combining Sulfonhydrazide Derivatization and Sulfonyl Derivatization

In this example, carbonyl protection via derivatization with a sulfahydrazide in combination with hydroxyl protection via derivatization with a sulfonyl halide allows the detection of both carbonyl and hydroxyl containing steroids, such as estrogens and androgens, and their metabolites. For example, only some endogenous estrogens and their metabolites possess a carbonyl functional group. In contrast, all endogenous estrogens and their metabolites have a phenolic or catechol A-ring. Addition to the hydroxyl of a highly ionizable moiety such as a dansyl group can be performed by reaction with a sulfonyl halide. Such a step will add the highly ionizable moiety to all endogenous estrogens, because all these estrogens have a hydroxyl group that can be derivatized by the reaction. In contrast, not all endogenous estrogens contain a carbonyl group, and in the absence of the carbonyl group they are not capable of being derivatized by the sulfonhydrazide. Derivatization with the sulfonhydrazide alone is therefore not able to derivatize all endogenous estrogens for the purpose of enhancing their API (such as ESI) efficiency and HPLC-ESI-MS method sensitivity at positive ion mode.

Although it is advantageous to perform sulfonyl derivatization of the hydroxyl groups of the endogenous steroids (such as estrogens or androgens), it is difficult to use such an approach with steroids that contain the carbonyl. The carbonyl group in D-ring ketolic steroid metabolites (such as estrogen) is alkali labile, and is readily destroyed or interconverted in an alkaline environment during the reaction with the sulfonyl halide. In this example, the inventors disclose protecting the carbonyl group in D-ring ketolic estrogen metabolites by reacting with a sulfonhydrazide to form a chemically stable hydrazone before carrying out the sulfonyl derivatization. This method allows the derivatization of the hydroxyl group while avoiding carbonyl degradation under the alkali conditions of the sulfonyl derivatization. This combined derivatization approach allows both the hydroxyl and carbonyl groups to be derivatized without altering the carbonyl groups of the steroids.

Examples of the sulfonhyrazide compound are listed in Example 2, and in a specific example is TSH.

The sulfonyl derivatizing agents (such as sulfonyl halides) useful for forming API-MS (such as ESI-MS) detectable derivatives of hydroxyl-containing compounds in this example have the structure

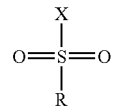

wherein X is Cl, Br, I, or any good leaving group, and R is any highly ionizable group that allow for the formation of ions under either the positive ion mode or the negative mode of ESI-MS, such as alkyl; substituted alkyl, aryl, and substituted aryl. In particular embodiments the alkyl is a lower alkyl (a C1-C10 alkyl, such as a C1-C5 alkyl).

In some embodiments, the sulfonyl derivatizing agent is a sulfonyl halide, such as a having the structure

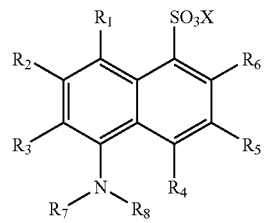

wherein X is Cl, Br, I, or any good leaving group, and R1-R8 are independently selected from the group consisting of hydrogen, C1-C5 alkyl, C1-C4 alkoxy, halogen, amino, nitro, hydroxyl, carbonyl, nitroso, cyano, and sulfonyl, and combinations thereof. In particular examples, R1-R6 are all hydrogen, and R7 and R8 are lower alkyl.

One example of a sulfonyl halide compound having this structure is a dansyl halide such as dansyl chloride which has the following chemical structure.

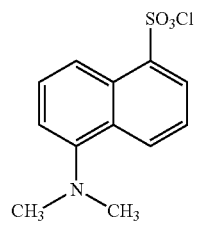

A. Chemicals and Reagents

Sixteen estrogens and estrogen metabolites (EM), as shown below, were obtained from Steraloids, Inc. (Newport, R.I., USA). Deuterium-labeled estrogens and estrogen metabolites (d-EM) were purchased from C/D/N Isotopes, Inc. (Pointe-Claire, Quebec, Canada). All EM and d-EM analytical standards have chemical and isotopic purity ≧98%, respectively, as reported by the manufacturers, and were used without further purifications.

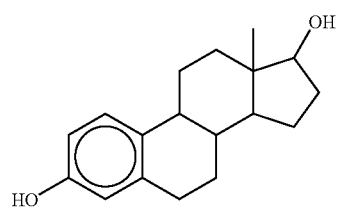

Estradiol

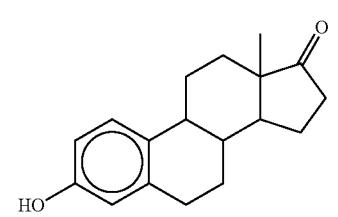

Estrone

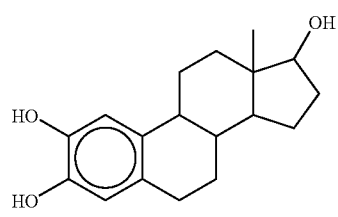

2-Hydroxyestradiol

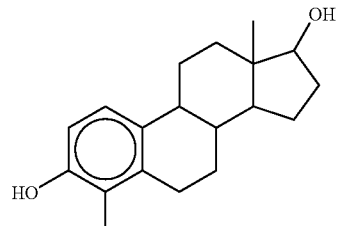

4-Hydroxyestradiol

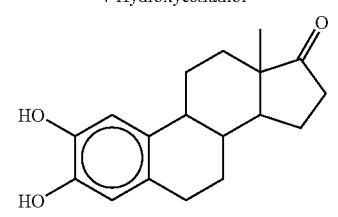

2-Hydroxyestrone

-continued

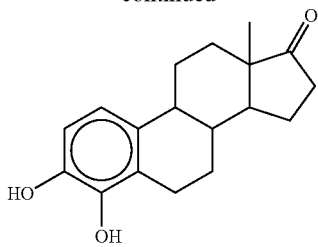

4-Hydroxyestrone

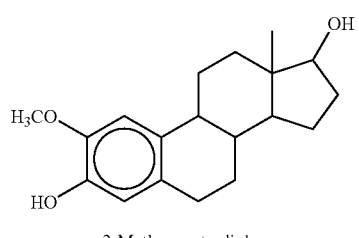

2-Methoxyestradiol

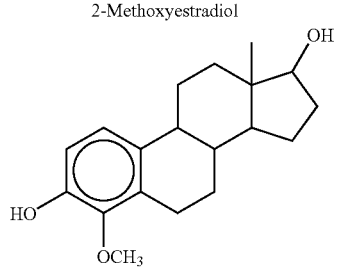

4-Methoxyestradiol

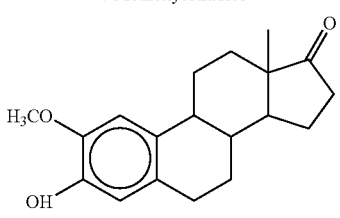

2-Methoxyestrone

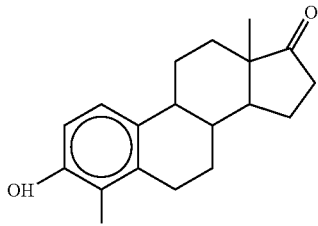

4-Methoxyestrone

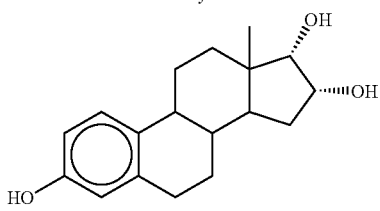

17-Epiestriol

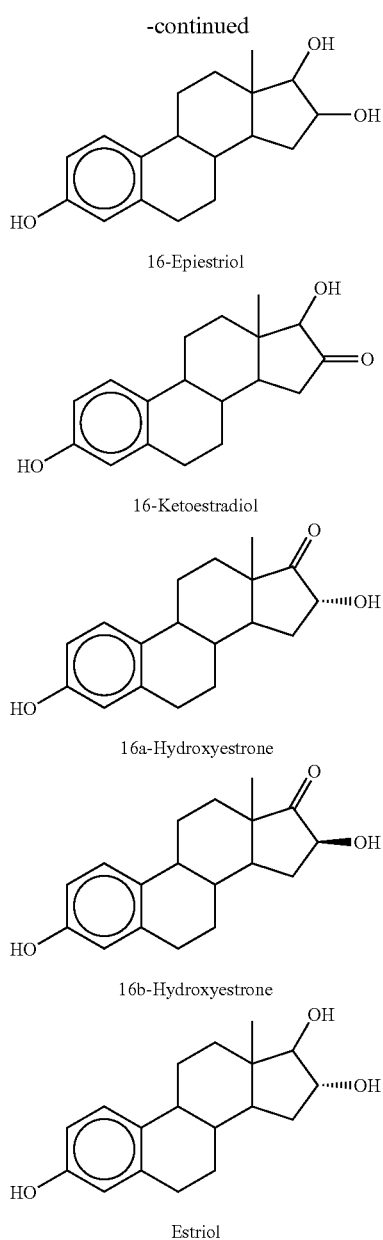

16-Epiestriol

16-Ketoestradiol

16a-Hydroxyestrone

16b-Hydroxyestrone

Estriol p-Toluenesulfonhydrazide (TSH), dansyl chloride, and acetone (HPLC grade) were purchased from Aldrich Chemical Co. (Milwaukee, Wis., USA). Methanol (HPLC grade) and formic acid (reagent grade) were obtained from EM Science (Gibbstown, N.J., USA), and water (HPLC grade) was obtained from Mallinckrodt Baker, Inc. (Paris, Ky., USA). Sodium bicarbonate (reagent grade) and sodium hydroxide (reagent grade) were purchased from J. T. Baker (Phillipsburg, N.J., USA).

B. Preparation of Stock and Working Standard Solutions

Stock solutions of EM and d-EM were prepared at 80 μg ml$^{-1}$ by addition of 2 mg individual estrogen powder to a volumetric flask and diluting to 25 ml with 100% methanol. These solutions were stored at −20° C. until needed to prepare working standard solutions. During each day of analysis, working standards of EM and d-EM were freshly prepared by serial dilutions of stock solutions with 100% methanol. In this example, d-EM working standard solution was prepared at 800 ng ml$^{-1}$, while EM working standard solutions were prepared at 800 and 50 ng ml$^{-1}$.

C. Derivatization Procedure

The methanolic solutions containing 8 ng of EM or d-EM was evaporated to dryness under nitrogen gas (Reacti-Vap III™, Pierce, Rockford, Ill., USA) and reacted with 400 μg p-toluenesulfonhydrazide in 200 μl methanol and heating at 60° C. (Reacti-Therm III™ Heating Module, Pierce, Rockford, Ill., USA) for 30 min (Xu et al. 2002, *J Chromatogr B*) to protect the carbonyl group. After TSH derivatization, estrogen samples were evaporated to dryness under nitrogen and redissolved in 70-μl of dansyl chloride solution (1 mg ml$^{-1}$ in acetone) and 30-μl of 50 mM sodium bicarbonate buffer (pH=10.5) and heated at 50° C. for 5 min (Yamada et al. 2000, *Biomed Chromatogr*).

For the purpose of comparison, the same EM or d-EM were derivatized with dansyl chloride procedure alone without prior protection of carbonyl group by TSH.

In both approaches, the reaction mixtures were directly injected for HPLC-ESI-MS analysis.

D. HPLC-ESI-MS

HPLC-ESI-MS analysis was performed on a Finnigan LCQ™ DECA ion trap mass spectrometer with Surveyor HPLC system (ThermoFinnigan, San Jose, Calif., USA) controlled by the Xcalibur™ software. Liquid chromatography was carried out on a reverse phase Luna C$_{18}$ column (150×2.0 mm, 3 μm; Phenomenex, Torrance, Calif., USA). The mobile phase consisted of methanol and water (85:15) with 0.1% (v/v) formic acid at the flow rate of 200 μl/min was used. Sensitivity was such that only 5 μl of each 100-μl sample was injected by autosampler for analysis. The entire chromatography effluent was passed into the mass spectrometer ESI interface for subsequent detection.

The ESI positive ion mode was used as follows: ion source voltage, 5 kV; heated capillary temperature, 250° C.; capillary voltage, 15 V; sheath gas flow rate, 70 units; auxiliary gas flow rate, 15 units; tube lens offset, 50 V. MS full scan mode was employed for characterizing mass spectra of both derivatization approaches.

E. Combining TSH Derivatization and Dansyl Halide Derivatization for Improved Signal Detection With combined sulfonhydrazide derivatization of the carbonyl and sulfonyl derivatization of the hydroxyl (with TSH and dansyl chloride respectively in this particular example), all estrogens and estrogen metabolites show intense protonated molecule [MH$^+$] and less abundant natriated molecule [MNa$^+$] during ESI positive ion mode. In contrast, some D-ring ketolic estrogen metabolites, such as 16α-hydroxyestrone, 16-ketoestradiol, 2-hydroxyestrone, and 4-hydroxyestrone, show rather poor response and hydrogen loss when derivatized with the dansyl chloride procedure alone without prior carbonyl protection (FIG. 8), which is believed to be due to their alkali labile nature. The extensive hydrogen loss found in deuterium-labelled D-ring ketolic estrogen metabolites with dansyl chloride derivatization alone is especially problematic since ion clusters from their protonated or natriated molecules also cover those of target analytes (FIGS. 8 and 9), which makes accurate quantitative measurement difficult.

Unlike the dansyl chloride derivatization alone, the combined TSH carbonyl protection and dansyl chloride derivatization is a method suitable for the quantitative measurement of all endogenous steroids (such as estrogens and estrogen metabolites) by HPLC-ESI-MS.

Example 9

General Approach to Combining Carbonyl and Hydroxyl Derivatization of Steroids In some more general embodiments, protecting the carbonyl group of the steroids allows for the derivatization of the hydroxyl group without significant steroid degradation. This two-step process of carbonyl derivatization followed by hydroxyl derivatization provides for better HPLC separation of steroids, and allows for better signal detection in API-MS (such as ESI-MS) when at least one of the derivatization groups contains a highly ionizable moiety that enables ionization under either positive ion or negative ion mode of electrospray ionization.

Examples of carbonyl protecting reagents that could be used in this two-step process include but are not limited to compounds that form an oxime derivative, silyl derivative, ketal/acetal, hydrazone, and Schiff's base derivative. Specific examples include methoxyamine, ethoxyamine, carboxymethoxylamine, Girard's Reagent T, Giard's Reagent P, 6-ethoxy-2-benzothiazolesulfonamide, cystein, N'-(2-Thiazolyl)sulfanilamide, sulfisomidine, sulfadiazine, and p-toluenesulfohydrazide (TSH).

Examples of hydroxyl protecting reagent that could be used in this two-step process includes but not limited to compounds that form silyl derivative, acyl derivative, benzoyl derivative, alkyl derivative, dansyl derivative, nitrobenzofuran derivative. Specific examples include nitrobenzopentaflurobenzoyl hydroxylamine, hydroxylamine, dabsyl chloride, and dansyl chloride, 1-fluoro-2,4-dinitrobenzene, and 4-fluoro-3nitrobenzofurazan.

In a particular specific example of this two step process, the carbonyl group in D-ring ketolic steroid metabolites (such as estrogen metabolites) is protected by forming a hydrazone, such as a chemically stable p-toluenesulfonhydrazone, before carrying out a dansyl halide derivatization (for example with dansyl chloride) under alkaline conditions.

For carbonyl, the most useful protective groups are the acyclic and cyclic acetals or ketals, and the acyclic and cyclic thioacetals or ketals. The carbonyl group can form a number of very stable derivatives such as cyanohydrins, hydrazones, imines, oximes, and semicarbazones, which is suitable for derivatization.

It should be recognized that the illustrated embodiments are only particular examples of the inventions and should not be taken as a limitation on the scope of the inventions. Rather, the inventions include all that comes within the scope and spirit of the following claims.

The invention claimed is:

1. A method for detecting ketosteroids, comprising:
    reacting a sample with a sulfonhydrazide to form a sulfonhydrazone of a ketosteroid in the sample;
    reacting the sulfonhydrazone with a sulfonyl halide; and
    analyzing the reacted sample by mass spectrometry to detect the ketosteroid by detecting the sulfonyl halide derivative of the sulfonhydrazone of the ketosteroid, wherein detection of the sulfonyl halide derivative of the sulfonhydrazone indicates presence of the ketosteroid.

2. The method of claim 1, wherein analyzing the sample by mass spectrometry comprises atmospheric pressure ionization.

3. The method of claim 2, wherein atmospheric pressure ionization comprises positive ion mode electrospray ionization.

4. The method of claim 1 further comprising separating the ketosteroid from other components in the sample by liquid chromatography.

5. The method of claim 4, wherein the liquid chromatography is high performance liquid chromatography (HPLC).

6. The method of claim 4, wherein the ketosteroid is reacted with the sulfonhydrazide prior to separating the ketosteroid by liquid chromatography.

7. The method of claim 5, wherein separating the ketosteroid from other components in the sample by HPLC comprises reverse phase HPLC using a non-polar stationary phase.

8. The method of claim 7 wherein reverse phase HPLC is performed using a methanol/water solvent.

9. The method of claim 7, wherein the non-polar stationary phase is a C18 stationary phase.

10. The method of claim 8, wherein HPLC is performed with gradient elution from 20:80 methanol/water to 80:20 methanol/water is used.

11. The method of claim 10, wherein gradient elution is performed from 40:60 methanol water to 60:40 methanol water is used.

12. The method of claim 1 further comprising extracting the ketosteroid from the sample prior to reacting the sample with the sulfonhydrazide to provide a concentrated sample for analysis.

13. The method of claim 1, wherein the ketosteroid is an estrogen.

14. The method of claim 13, wherein the ketosteroid is a catechol estrogen.

15. The method of claim 1, wherein the sulfonhydrazide is p-toluenesulfonylhydrazide.

16. The method of claim 1, wherein the sulfonyl halide comprises

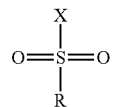

wherein X is Cl, Br, or I, and R is alkyl, substituted alkyl, aryl, or substituted aryl.

17. The method of claim 16, wherein R comprises lower alkyl.

* * * * *